United States Patent
DeShazo et al.

(10) Patent No.: US 11,969,600 B2
(45) Date of Patent: Apr. 30, 2024

(54) NEUROSTIMULATOR OUTPUT SWITCHING CIRCUITRY WITH SELF-TEST MODE

(71) Applicant: ADVANCED NEUROMODULATION SYSTEMS, INC., Plano, TX (US)

(72) Inventors: Daran DeShazo, Lewisville, TX (US); Gavin Rade, Dallas, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 125 days.

(21) Appl. No.: 17/355,677

(22) Filed: Jun. 23, 2021

(65) Prior Publication Data
US 2022/0409911 A1    Dec. 29, 2022

(51) Int. Cl.
| | | |
|---|---|---|
| A61N 1/372 | (2006.01) | |
| A61B 5/367 | (2021.01) | |
| A61N 1/36 | (2006.01) | |
| A61N 1/362 | (2006.01) | |
| A61N 1/378 | (2006.01) | |
| A61N 1/38 | (2006.01) | |
| A61N 1/39 | (2006.01) | |
| A61N 2/00 | (2006.01) | |

(52) U.S. Cl.
CPC ..... *A61N 1/37235* (2013.01); *A61N 1/37223* (2013.01); *A61N 1/378* (2013.01); *A61B 5/367* (2021.01); *A61N 1/36038* (2017.08); *A61N 1/36053* (2013.01); *A61N 1/36062* (2017.08); *A61N 1/36082* (2013.01); *A61N 1/362* (2013.01); *A61N 1/38* (2013.01); *A61N 1/39622* (2017.08); *A61N 2/006* (2013.01)

(58) Field of Classification Search
CPC ............ A61N 1/37235; A61N 1/37223; A61N 1/378; A61N 1/367; A61N 1/36038; A61N 1/36053; A61N 1/36062; A61N 1/36082; A61N 1/362; A61N 1/38; A61N 1/39622; A61N 2001/37294
See application file for complete search history.

(56) References Cited

U.S. PATENT DOCUMENTS

| | | | |
|---|---|---|---|
| 7,212,110 B1 | 5/2007 | Martin et al. | |
| 7,228,179 B2 | 6/2007 | Campen et al. | |
| 7,450,987 B2 * | 11/2008 | Varrichio | ................ H02M 3/07 607/2 |
| 7,571,007 B2 | 8/2009 | Erickson et al. | |
| 8,446,212 B2 | 5/2013 | Tranchina et al. | |

(Continued)

FOREIGN PATENT DOCUMENTS

WO    2001/093953 A1    12/2001

*Primary Examiner* — Brian T Gedeon
(74) *Attorney, Agent, or Firm* — Norton Rose Fulbright US LLP

(57) ABSTRACT

An implantable medical device (IMD) includes one or more stimulation engines (SEs) and selectively connectable output switching circuitry for driving a plurality of output nodes associated with a respective plurality of electrodes of the IMD's lead system when implanted in a patient. The output switching circuitry may be configured to facilitate self-test mode (STM) functionality in the IMD (e.g., when it is in a hermetically sealed package) by using a dual mode switch in series with a stimulation engine selection switch with respect to each output node in the output switching circuitry under mode selection control.

9 Claims, 17 Drawing Sheets

(56) References Cited

U.S. PATENT DOCUMENTS

| | | |
|---|---|---|
| 9,844,661 B2 | 12/2017 | Franz et al. |
| 10,894,159 B2 | 1/2021 | De Ridder |
| 2006/0170486 A1 | 8/2006 | Tranchina et al. |
| 2009/0048643 A1 | 2/2009 | Erickson et al. |
| 2009/0326608 A1 | 12/2009 | Huynh et al. |
| 2011/0072657 A1 | 3/2011 | Swanson et al. |
| 2014/0343564 A1 | 11/2014 | Feler et al. |
| 2018/0008821 A1 | 1/2018 | Gonzalez et al. |
| 2020/0246619 A1* | 8/2020 | Foreman .................. G05F 1/56 |
| 2020/0316390 A1* | 10/2020 | Swenson ............ A61N 1/37217 |
| 2021/0252291 A1* | 8/2021 | DeShazo ............ A61N 1/36171 |

* cited by examiner

NEUROSTIMULATOR OUTPUT SWITCHING CIRCUITRY WITH SELF-TEST MODE

TECHNICAL FIELD

The present disclosure generally relates to implantable medical devices (IMDs). More particularly, and not by way of any limitation, the present disclosure is directed to IMDs having output switching circuitry for facilitating self-test mode functionality.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Depending on implementation, all or a portion of a stimulation system may not be implanted into a body to provide a desired therapy.

A stimulation system pulse generator may be provided in various configurations, such as a totally implanted pulse generator (IPG) or a radio frequency (RF)-based system. An example IPG configuration may comprise a surgically implanted, internally-powered pulse generator and one or more multi-electrode leads. An example RF system configuration may comprise a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Applying low-amplitude stimulation parameters can also "mask" pain or other symptoms without producing "paresthesia" in some arrangements (e.g., a sub-paresthesia therapy system). Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Whereas advances in IPG/IMD systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to IMDs having one or more stimulation engines and selectively connectable output switching circuitry for driving a plurality of output nodes associated with a respective plurality of electrodes of an IMD's lead system. The output switching circuitry may be configured to facilitate self-test mode (STM) functionalities in an IMD that is in a hermetically sealed package, e.g., in transit or storage. In STM, example embodiments herein allow accessing the IMD via a wireless communication link for actuating at least a portion of the output switching circuitry in a selectable manner to effectuate one or more internal circuit paths that may be used by a measurement circuit for testing the integrity and performance of switch elements and pulse current programmability although the IMD is not connected to an external load such as, e.g., a patient's tissue.

In one aspect, an embodiment of the present patent disclosure is directed to an IMD, which comprises, inter alia, a power supply; one or more processors; communication circuitry operative to effectuate a machine-to-machine (M2M) communication link with an external device using a wireless communication protocol; a voltage multiplier (VM) configured to generate an adjustable target voltage at a VM node based on a voltage supplied by the power supply; at least one stimulation engine operative to energize at least a portion of a plurality of electrodes of a lead system when implanted proximate to a tissue of a patient; and output switching circuitry operative to drive a plurality of output nodes, each output node connectable to a corresponding electrode of the plurality of electrodes when implanted in the patient. In one arrangement, the output switching circuitry comprises, for each respective output node, a switching element portion that includes a dual mode (DM) switch for selectively coupling (e.g., as a first switch) the respective output node to the VM node operative to power an anodic node of the at least one stimulation engine; and one or more stimulation engine selection (SES) switches operative to be disposed in a series connection with the DM switch. A select one of the one or more SES switches may be configured for selectively coupling (e.g., as a second switch) the respective output node to a cathodic node of the at least one stimulation engine, wherein the DM switch and the select one of the one or more SES switches are activated to close so as to effectuate an internal circuit path in the output switching circuitry of the IMD in a self-test mode in response to one or more digital control signals generated under control of the one or more processors operating responsive to a mode selection control signal from the external device, e.g., while the IMD is disposed in a sealed package condition.

In one arrangement, an example IMD may comprise a programmable measurement circuit having selectable inputs operative to effectuate one or more measurement loops involving at least a portion of an internal circuit path via the output switching circuitry when the IMD is in self-test mode. Example measurement loops may comprise, for each respective output node of the output switching circuitry, a measurement path across at least one of the DM switch in a closed state and the select one of the one or more SES switches in a closed state. In one arrangement, the programmable measurement circuit may be configured to measure, for each respective output node, at least one of an impedance of the DM switch in the closed state, an impedance of the select one of the one or more SES switches in the closed state, or both, and/or programmability of a pulse current through the measurement path, the pulse current having one or more configurable pulse settings and patterns selectable from a user interface of the external device.

In another aspect, an embodiment of the present patent disclosure is directed to a method operative with an IMD for effectuating STM functionality, e.g., while disposed in a sealed package. The example method comprises, inter alia, establishing a machine-to-machine (M2M) communication link with an external device; responsive to a mode selection control signal received from the external device, generating one or more digital control signals for effectuating one or more internal circuit paths via the IMD's output switching circuitry by selectively activating a DM switch and a select SES switch of a plurality of SES switches associated with each output node of the output switching circuitry, wherein the plurality of SES switches are respectively operative with a corresponding plurality of SEs and each output node is operative to be connected to a corresponding electrode of a plurality of electrodes of a lead system when implanted proximate to a patient's tissue; and selectively coupling a programmable measurement circuit to at least a portion of an internal circuit path associated with a particular output node to measure at least one of an impedance of a DM switch associated with the particular output node, an impedance of a select SES switch associated with the particular output node, or both, and/or programmability of a pulse current through a measurement path forming the at least a portion of the internal circuit path, wherein the DM and SES switches associated with the particular output node are disposed in respective closed states forming part of the measurement path in a series connection. In one arrangement, a test pulse current through the measurement path may be programmed to have one or more configurable pulse settings and patterns selectable from the external device. In one arrangement, one or more measurements obtained from the programmable measurement circuit may be provided to the external device for presentation via a user interface associated therewith. In one arrangement, the mode selection control signal may be received from the external device comprising one of a clinician programmer device, a field technician device (e.g., having a lower or subordinate level of authorization) and an IMD manufacturer tester device operative to test a field-returned device in its sealed package. In one arrangement, an STM disable signal may be received from the external device, e.g., after implanting the IMD and associated lead system in a patient. Responsive to the STM disable signal, the formation of an internal circuit path may be inactivated or otherwise electrically hindered in the IMD's output switching circuitry with respect to each output node of the output switching circuitry.

In one arrangement, an example method of operating an IMD may comprise, inter alia, configuring the IMD to operate in a stimulation mode after the IMD is implanted in the patient; configuring a first electrode as an anode; coupling the first electrode to a VM node by activating a DM switch associated with the first electrode to be in a closed state; activating an SES switch associated with the first electrode to be in an open state; configuring a second electrode as a cathode; activating a DM switch associated with a second electrode to be in an open state; coupling the second electrode to a cathodic node of a particular one of the plurality of stimulation engines by activating an SES switch associated with the second electrode to be in a closed state; and causing to energize, responsive to enabling a pulse signal, the first and second electrodes to provide stimulation therapy to the patient.

In one arrangement, an example method of operating an IMD may comprise, inter alia, configuring the IMD to operate in a discharge mode after providing stimulation therapy to the patient via first and second electrodes, the discharge mode involving disabling of a pulse signal and/or providing a discharge enable signal; activating a DM switch associated with the first electrode to be in an open state, thereby disconnecting the first electrode from a VM node; and activating an SES switch associated with the first electrode to be in a closed state to couple to the cathodic node of the particular one of the at least one stimulation engine while an SES switch associated with the second electrode remains in the closed state, thereby continuing to maintain an electrical connection between the second electrode and the cathodic node of the particular one of the at least one stimulation engine. As both first and second electrodes are commonly connected, a passive discharge operation may be effectuated without requiring additional/dedicated switching circuitry for discharging the electrodes after stimulation. Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
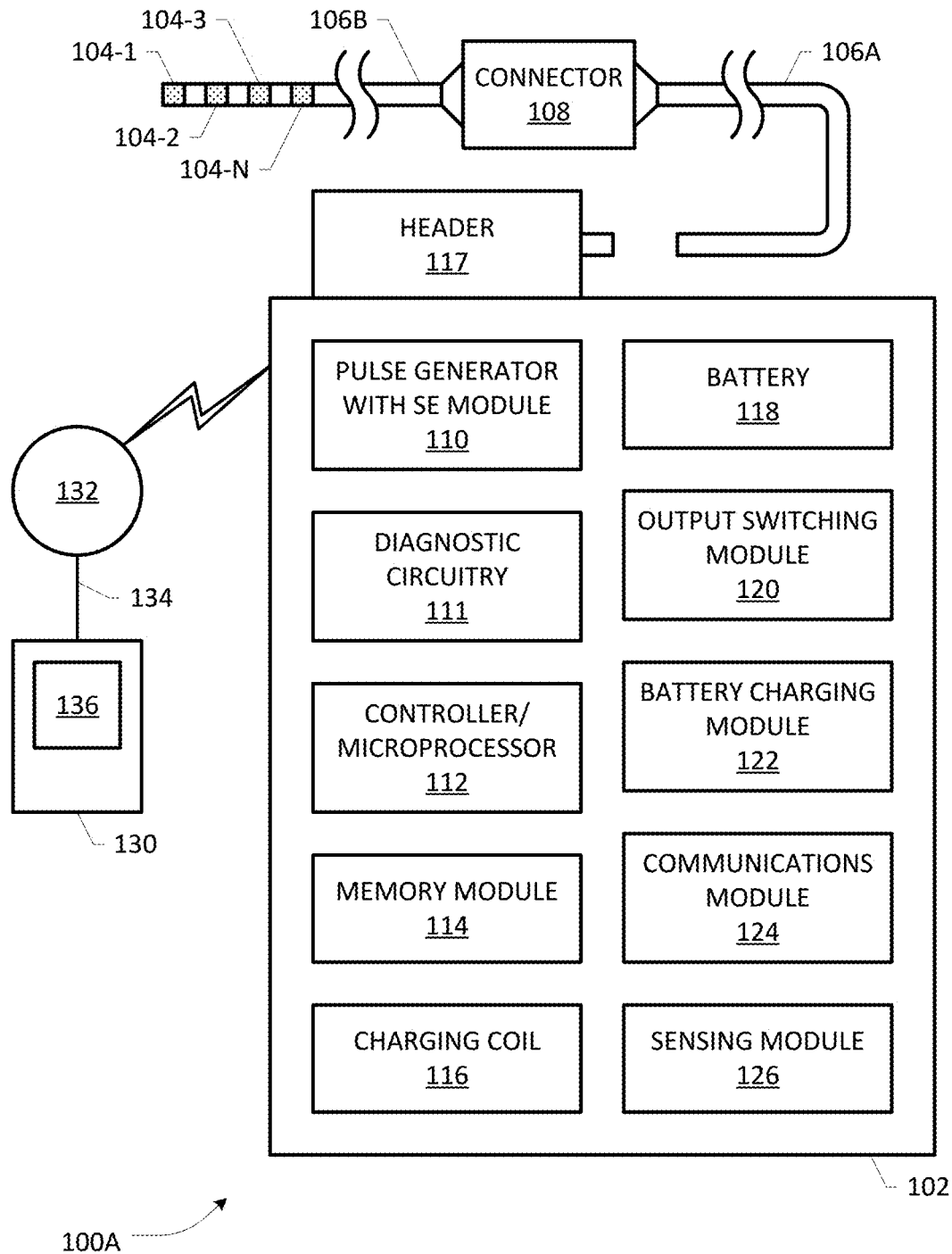
FIG. 1A depicts an example biostimulation system wherein an embodiment of an implantable medical device (IMD) having one or more stimulation engines (SEs) may be tested in a self-test mode (STM) according to the teachings herein.

In the description herein for embodiments of the present disclosure, numerous specific details are provided, such as examples of circuits, devices, components, and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) that may be configured to provide, when implanted proximate to a patient's tissue, suitable electrical stimulation according to one or more stimulation sets for application to a desired target area based on a particular therapy application such as a spinal cord stimulation (SCS) system. However, it should be understood that example circuitry and methods of operation, including example output switching circuitry for facilitating self-test mode (STM) functionality as disclosed herein, are not limited thereto but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia. Still further, whereas some example embodiments of therapy applications may involve implantable devices that may be tested while in a sealed package condition, additional and/or alternative embodiments may involve external personal devices, e.g., wearable biomedical devices, that may be configured to provide therapy to the patients analogous to the implantable devices, which may also be tested in a package condition by invoking a suitable STM functionality via another external device. It should therefore be appreciated that regardless of whether a personal medical therapy device is implantable or externally disposed for providing therapy to a patient, such a device may be provided with output switching circuitry of the present disclosure for facilitating STM functionality according to the teachings set forth herein.

Figure 12:
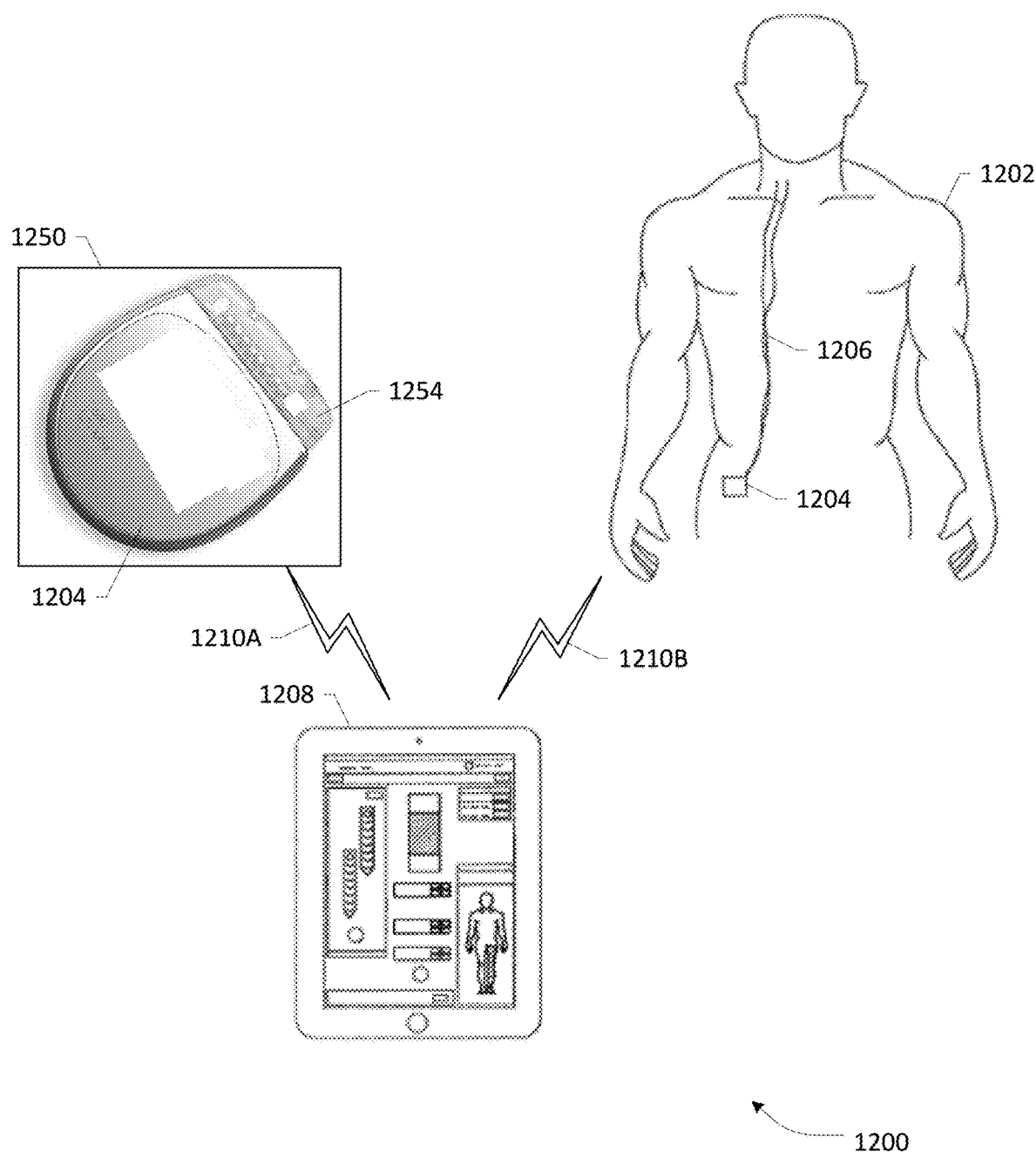
FIG. 12 depicts an example system wherein an external device is operative to effectuate mode control to select a self-test mode functionality with respect to an IMD that is in a sealed package or a therapy and discharge mode functionality when the IMD and associated lead system is implanted in a patient according to some embodiments of the present disclosure.

Without limitation, example embodiments will be described in detail in the context of IMDs/IPGs operative to provide various types of stimulation therapy, wherein STM functionality may be selectively activated or deactivated by appropriate user interfacing when an IMD is disposed in a packaged condition and/or deployed in a patient as an implanted device. Referring to FIG. 12 in particular, depicted therein is an example system 1200 wherein an external device 1208 having a suitable application or program executing thereon is operative to effectuate mode control to select STM functionality with respect to an IMD 1204 that is in a sealed package 1250 (e.g., hermetically sealed) or a therapy and discharge mode (TDM) functionality when IMD 1204 and associated lead system 1206 is implanted in a patient 1202 according to some embodiments of the present disclosure. System 1200 is illustrative of an arrangement wherein external device 1208 may be operated by a user, e.g., a clinician, a field medical technician, patient 1202 and/or an authorized agent respectively thereof having appropriate level(s) of privilege authorization, to administer and activate different functionalities relative to self-testing and/or providing therapy by communicating with IMD 1204 via suitable communication links 1210A/B depending on whether IMD 1204 is in a sealed package state or in implanted state. External device 1208 may comprise commercial off-the-shelf (COTS) equipment such as a portable computer, smartphone, tablet, phablet, laptop, or the like, or a proprietary portable medical/healthcare device, which may be configured to execute a therapy application program or other type of software, generally referred to as an "app", that may be invoked via a suitable user interface, e.g., a graphic UI (GUI), a voice-based UI, etc., wherein various types of communications relating to mode selection control, therapy/diagnostics, and/or test program and stimulation program management may be effectuated between one or more modules of external device 1208 and IMD 1204. After IMD 1204 is removed from the sealed package 1250, IMD 1204 may be implanted within the patient 1202 at a suitable location, e.g., proximate to the spinal cord or other tissue or organ depending on the therapy, wherein one or more leads 1206 having one or more electrodes and/or sensors (not specifically shown in this FIG.) coupled to a header portion 1254 of IMD 1204 may be activated to provide therapy and/or obtain measurement information. Additionally or alternatively, IMD 1204 may have components that are external to the patient 1202; for example, IMD 1204 may be associated with an external pulse generator (EPG) or other non-invasive personal medical devices (PMDs) that may also be configured to provide therapy and/or obtain test measurement data.

In one arrangement, external device 1208 may be configured to establish appropriate wireless telemetry and communication links with IMD 1204 that may be operative to effectuate different levels or types of IMD functionalities depending on whether or not IMD 1204 is implanted in addition to the authorization levels of the device users and application programs executing on external device 1208. For example, a limited functionality may be effectuated via a bi-directional communication link 1210A for invoking STM when IMD 1204 is in its sealed package condition, wherein one or more mode selection control signals may be provided to IMD 1204 for facilitating testing of certain structural and functional components of IMD 1204 although output nodes of IMD 1204 are not connected to the patent tissue or an external load. After the implantation of IMD 1204 and associated lead system in patient 1202, a bi-directional communication link 1210B between external device 1208 and IMD 1204 may be effectuated for facilitating a broader range of control signaling and data communications with respect to therapy applications, discharge modalities as well as therapy measurements, exchange of sensory data, personal data, logging data, etc. In one arrangement, bi-directional communication links 1210A/B may be effectuated via a wireless personal area network (WPAN) using a standard wireless protocol such as Bluetooth Low Energy (BLE), Bluetooth, Wireless USB, Zigbee, Near-Field Communications (NFC), WiFi (e.g., IEEE 802.11 suite of protocols), Infrared Wireless, and the like. In some arrangements, communication links 1210A/B may also be established using magnetic induction techniques rather than radio waves, e.g., via an induction wireless mechanism. Alternatively and/or additionally, communication links 1210A/B may be effectuated in accordance with certain healthcare-specific communications services including, Medical Implant Communication Service (MICS), Wireless Medical Telemetry Service (MTS), Medical Device Radiocommunications Service (MDRS), Medical Data Service (MDS), etc. Accordingly, regardless of which type(s) of communication technology being used, external device 1208 and IMD 1204 may each be provided with appropriate hardware, software and firmware (e.g., forming suitable communication circuitry including transceiver circuitry and antenna circuitry where necessary) for effectuating communication links 1210A/B, along with corresponding protocol stacks executing on respective device platforms. In some implementations, therefore, wireless telemetry communications between external device 1208 and IMD 1204 may be effectuated as machine-to-machine (M2M) communications based on appropriate protocols. Furthermore, external device 1208 and IMD 1204 may each be provisioned with suitable security credential information that may be used for facilitating application-specific authentication and authorization as an overlay layer in some embodiments for facilitating appropriate modes of IMD operations according to the teachings herein.

Figure 13:
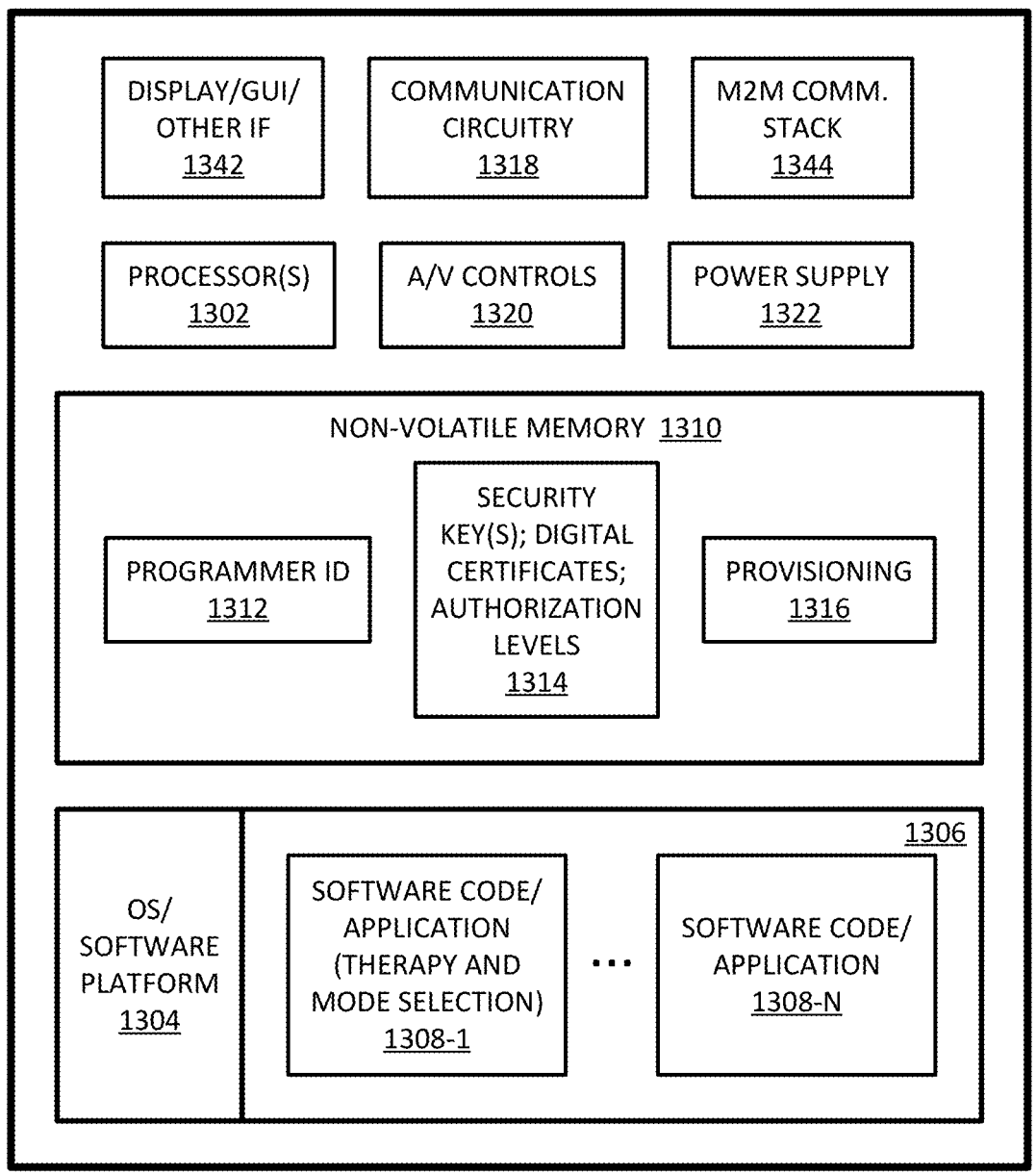
FIG. 13 depicts a block diagram of an external device according to an example embodiment of the present patent disclosure.

FIG. 13 depicts a block diagram of an external device 1300 according to an example embodiment of the present patent disclosure that may be configured with an application program operative to execute self-test functionality, therapy functionality, or both, with respect to an IMD. For example, depending on configuration and/or modality, external device 1300 may be representative of a clinician programmer device, a patient controller device, a delegated device operated by an agent of a patient or a clinician having subordinate levels of privilege authorization with respect to a therapy/test application, or a field/service technician device having limited authorization to conduct self-test operations. Further, external device 1300 may be a COTS device or non-COTS device as previously noted. Still further, external device 1300 may be a device that is controlled and managed in a centralized enterprise device management system (EDMS), also referred to as a mobile/medical device management system (MDMS), which may be associated with the manufacturer of the IMDs and associated therapy application components in some embodiments (e.g., as an intranet implementation, an extranet implementation, or internetbased cloud implementation, etc.), in order to ensure that only appropriately managed/provisioned devices and users are allowed to engage in communications with IMDs with respect to testing the devices and/or providing therapy to patients using approved therapy applications.

Still further, external device 1300 may be a device that is not controlled and managed in such a device management system. Accordingly, it will be realized that external device 1300 may comprise a device that may be configured in a variety of ways depending on how its functional modality is implemented in a particular deployment. Regardless of the myriad combinations, an example embodiment of external device 1300 may be configured to provide a suitable interface to a user upon establishing a communication link with an IMD for selecting STM functionality and performing one or more test programs with respect to various structural and functional components of the IMD (e.g., in a sealed package and/or in an implanted state).

Example external device 1300 may include one or more processors 1302, communication circuitry 1318 and one or more memory modules 1310, operative in association with one or more OS platforms 1304 and one or more software applications 1308-1 to 1308-K depending on configuration, cumulatively referred to as software environment 1306, and any other hardware/software/firmware modules, all being powered by a power supply 1322, e.g., battery. Example software environment 1306 and/or memory 1310 may include one or more persistent memory modules comprising program code or instructions for controlling overall operations of the device, inter alia. Example OS platforms may include embedded real-time OS systems, and may be selected from, without limitation, iOS, Android, Chrome OS, Blackberry OS, Fire OS, Ubuntu, Sailfish OS, Windows, Kai OS, eCos, LynxOS, QNX, RTLinux, Symbian OS, VxWorks, Windows CE, MontaVista Linux, and the like. In some embodiments, at least a portion of the software applications may include code or program instructions operative as a medical application having therapy and/or test modes, e.g., application 1308-1, which may be configured to interoperate with program code stored in memory 1310 to execute various operations relative to device registration, mode selection, test programming, therapy programming, security applications, and provisioning, etc., as part of a device controller application. Further, application 1308-1 may include code or program instructions configured to effectuate wireless telemetry and authentication with an IMD using a suitable M2M communication protocol stack, e.g., stack 1344, which may be mediated via virtual/digital assistant technologies in some arrangements.

In some embodiments of external device 1300, memory modules 1310 may include a non-volatile storage area or module configured to store relevant patient data, therapy settings, and the like. Memory modules 1310 may further include a secure storage area 1312 to store a device identifier (e.g., a serial number) of device 1300 used during testing sessions and/or therapy sessions (e.g., local therapy programming or remote therapy programming). Also, memory modules 1310 may include a secure storage area 1314 for storing security credential information, e.g., one or more cryptographic keys or key pairs, signed digital certificates, etc., having various levels of authorization, which may be associated with users (e.g., clinicians, patients, respective agents, authorized field technicians and the like), certificates of trusted provisioning entities, etc. In some arrangements, such security credential information may be specifically operative in association with approved/provisioned software applications, e.g., therapy/test application 1308-1, which may be obtained during provisioning. Communication circuitry 1318 may include appropriate hardware, software and interfaces to facilitate wireless and/or wireline communications, e.g., inductive communications, wireless telemetry or M2M communications, etc. to effectuate IMD communications, as well as networked communications with cellular telephony networks, local area networks (LANs), wide area networks (WANs), packet-switched data networks, etc., based on a variety of access technologies and communication protocols. External device 1300 may also include appropriate audio/video controls 1320 as well as suitable display(s) (e.g., touch screen), camera(s), microphone, and other user interfaces (e.g., GUIs) 1342, which may be utilized for purposes of some example embodiments of the present disclosure, e.g., facilitating user input, initiating IMD communications, mode selection, therapy selection, etc., including selection of different combinations of output nodes of the IMD's output switching circuitry for testing different components of the IMD using suitable test programs.

Turning now to FIG. 1A, depicted therein is a biostimulation system 100A wherein an embodiment of an IMD having one or more stimulation engines (SEs) may be tested according to the teachings herein, e.g., while the IMD is disposed in a sealed package condition. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. In one arrangement, system 100A may comprise an implantable pulse generator (IPG) or IMD 102 having a pulse generator portion that may include one or more SEs adapted to provide independent therapies to different sets of electrodes of a lead system when implanted in a patient.

In one example embodiment, IMD 102 may be implemented as having a metallic housing or can that encloses a controller/processing block or module 112, pulse generating circuitry 110 including one or more SEs, a charging coil 116, a battery/power supply 118, a far-field and/or near field communication block or module 124, battery/power supply charging circuitry 122, output switching circuitry 120, sensing circuitry 126, memory module(s) 114, and the like. Controller/processor module 112 typically includes a microcontroller or other suitable processor for controlling the various other components of IMD 102. Software/firmware code may be stored in memory 114, which may be integrated with the controller/processor module 112, and/or other suitable application-specific storage components (not particularly shown in this FIG.) for execution by the microcontroller or processor 112 and/or other programmable logic blocks to control the various components of IMD 102 for purposes of an embodiment of the present patent disclosure. As will be set forth below, output switching circuitry or module 120 may include a switch matrix comprising a plurality of switch elements depending on the number of SEs and output nodes provided as part of IMD 102, wherein various sets or subsets of the switch elements may be selectively activated and deactivated in different permutations and/or combinations responsive to determining whether IMD 102 is operated in STM functionality (e.g., when disposed in a sealed package) or in normal TDM functionality (e.g., after implanted in a patient and the STM functionality is selectively/optionally disabled).

In one arrangement, IMD 102 may be coupled to a separate or an attached extension component 106A for providing electrical and physical connectivity to a lead system via a lead connector 108 when implanted, wherein one or more leads each having a respective plurality of electrodes may be provided. By way of example, a single lead 106B is illustrated, wherein a distal end of the single lead 106B includes a plurality of electrodes 104-1 to 104-N, which in one embodiment may respectively correspond to a plurality of output nodes driven by the output switching module 120. Extension component 106A may connect with a header 117 of IPG/IMD 102 as is known in the art. If the extension component 106A is integrated with IMD 102, internal electrical connections may be made through respective conductive components. In general operation, electrical pulses are generated by one or more SEs of the pulse generating circuitry 110 under the control of processing block 112, and are provided to the output switching circuitry 120 that is operative to selectively connect to electrical outputs of the IMD (i.e., output nodes), which are ultimately coupled to electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B (e.g., deployed as a percutaneous lead). Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may comprise one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference. Further, it should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERING THE SAME", which is incorporated herein by reference.

In one arrangement, the lead system 106B (including extension 106A where provided) may comprise a lead body of insulative material encapsulating a plurality of conductors within the material that extend from a proximal end (that is proximate to IMD 102) to the distal end of the lead body containing electrodes 104-1 to 104-N. The conductors or conductive traces are operative to electrically couple electrodes 104-1 to 104-N to a corresponding plurality of terminals (not shown) of the lead system 106A/B. In general, the terminals are adapted to receive electrical pulses from the pulse generation and switching circuitry of IMD 102 via a set of output nodes driven by the output switching circuitry 120, which are propagated by the corresponding conductive traces to at least a corresponding portion of electrodes 104-1 to 104-N that are adapted to apply the pulses to a desired stimulation target of the patient depending on the particular stimulation therapy application. Also, sensing of physiological or bioelectrical signals may occur in some embodiments through lead electrodes 104-1 to 104-N, corresponding conductors, and associated terminals. By way of further illustration, an example embodiment of the stimulation system 100A may be provided with one or more leads, each having a plurality of lead electrodes 104-1 to 104-N comprising four electrodes, eight electrodes, etc., although any suitable number of electrodes (as well as corresponding conductive traces and terminals) may be provided, wherein the leads may be configured to be positioned proximate to a patient's tissue at one or more locations for providing appropriate stimulation therapy/therapies by activating/deactivating suitable output switching portions after implant. Additionally, alternatively, or optionally, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IMD 102, such as, e.g., processor and associated charge control circuitry for pulse generation, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IMD using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. In some embodiments, one or multiple sets of such circuitry may be provided for operation in association with respective current regulation circuitry as part of individual stimulation engines of module 110 for independently energizing different portions or sets of the electrodes of the lead system. In some example embodiments, different stimulation pulses on different lead electrodes selected from electrodes 104-1 to 104-N may be generated according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that may include selective stimulation therapy treatments through one or more leads or electrodes 104-1 to 104-N as is also known in the art. Various sets of parameters may define the pulse characteristics and pulse timing for the pulses applied to the various lead electrodes as is known in the art. It should be appreciated that although constant current pulse generating circuitry is set forth with respect to some embodiments, any other suitable type of pulse generating circuitry may be employed in association with the output switching circuitry arrangement of the present disclosure wherein different combinations of switch elements may be selectively activated or deactivated depending on selected modality for conducting IMD operations.

An external device 130 may be implemented to charge/recharge the battery/power supply 118 of IMD 102 (although a separate recharging device could alternatively be employed), to access memory 114, and/or to program or reprogram IMD 102 with respect to conducting STM operations as well as normal TDM operations, which may include applying various stimulation set parameters and pulsing/discharge specifications depending on whether IMD 102 is implanted within the patient or still in a sealed package. In alternative embodiments, however, separate programmer devices may be employed for charging and/or programming IMD 102 device and/or any programmable components thereof. Accordingly, external device 130 may be configured to effectuate only STM operations with respect to IMD 102 when IMD 102 is not implanted in the patient, or a combination of TDM and STM operations or just TDM operations while IMD 102 is within the patient, as noted above with respect to FIGS. 12 and 13.

An example embodiment of external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc., as previously set forth. Software may be stored within a non-transitory memory of the external device 130, which may be executed by the processor to control the various operations of the external device 130. In some arrangements, a connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IMD 102. Alternatively, there may be no separate or additional external communication/telemetry components provided with external device 130 in an example embodiment for facilitating bi-directional communications with IMD 102 (e.g., based on BLE).

In some arrangements, a user (e.g., a doctor, a medical technician, or the patient) may initiate communication with IMD 102 by placing wand 134 proximate to or within the stimulation system 100A. Preferably, the placement of wand 134 allows the telemetry system to be aligned with the far-field and/or near field communication circuitry 124 of IMD 102. External device 130 preferably provides one or more user interfaces (I/Fs) 136 (e.g., touch screen, keyboard, mouse, buttons, scroll wheels or rollers, or the like), allowing the user to operate IMD 102. External device 130 may be controlled by the user through the user interface 136, allowing the user to interact with IMD 102, including, e.g., effectuating mode selection as well as providing programmatic control for dynamically configuring stimulation current pulses and test current pulses in combination with independent selection/activation of different stimulation engines and output nodes (and corresponding electrodes) in some embodiments. Further, user interface 136 may permit the user to move electrical stimulation along and/or across one or more of the lead(s) 106A/B using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which sets or subsets of electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally, some electrodes of the lead system 106/A/B may be configured to operate as current sink terminals or cathodes whereas other electrodes may be configured as current source terminals or anodes. Accordingly, it will be realized that the plurality of output nodes driven by output switching circuitry 120 of IMD 102 may be selectively configured as anodes, cathodes or floating nodes while conducting STM operations with respect to IMD 102 that is still in a sealed package.

Regardless of whether STM or TDM operations are engaged, various test and/or therapy programs may be effectuated by operating external device 130 to interact with IMD 102, wherein a program may include one or more sets of configurable pulse settings, characteristics, parameters and patterns, e.g., including pulse amplitude, stimulation level, pulse width, pulse frequency or inter-pulse period, pulse repetition parameter (e.g., number of times for a given pulse to be repeated for respective stimulation sets or stimsets during execution of program), biphasic pulsing, monophasic pulsing, etc. In some embodiments, test mode programming may be selectively enabled or disabled by requiring a check register or a multi-bit write operation to ensure that STM can only be entered intentionally by the user regardless of whether IMD 102 is implanted or is still within a sealed package.

Figure 1B:
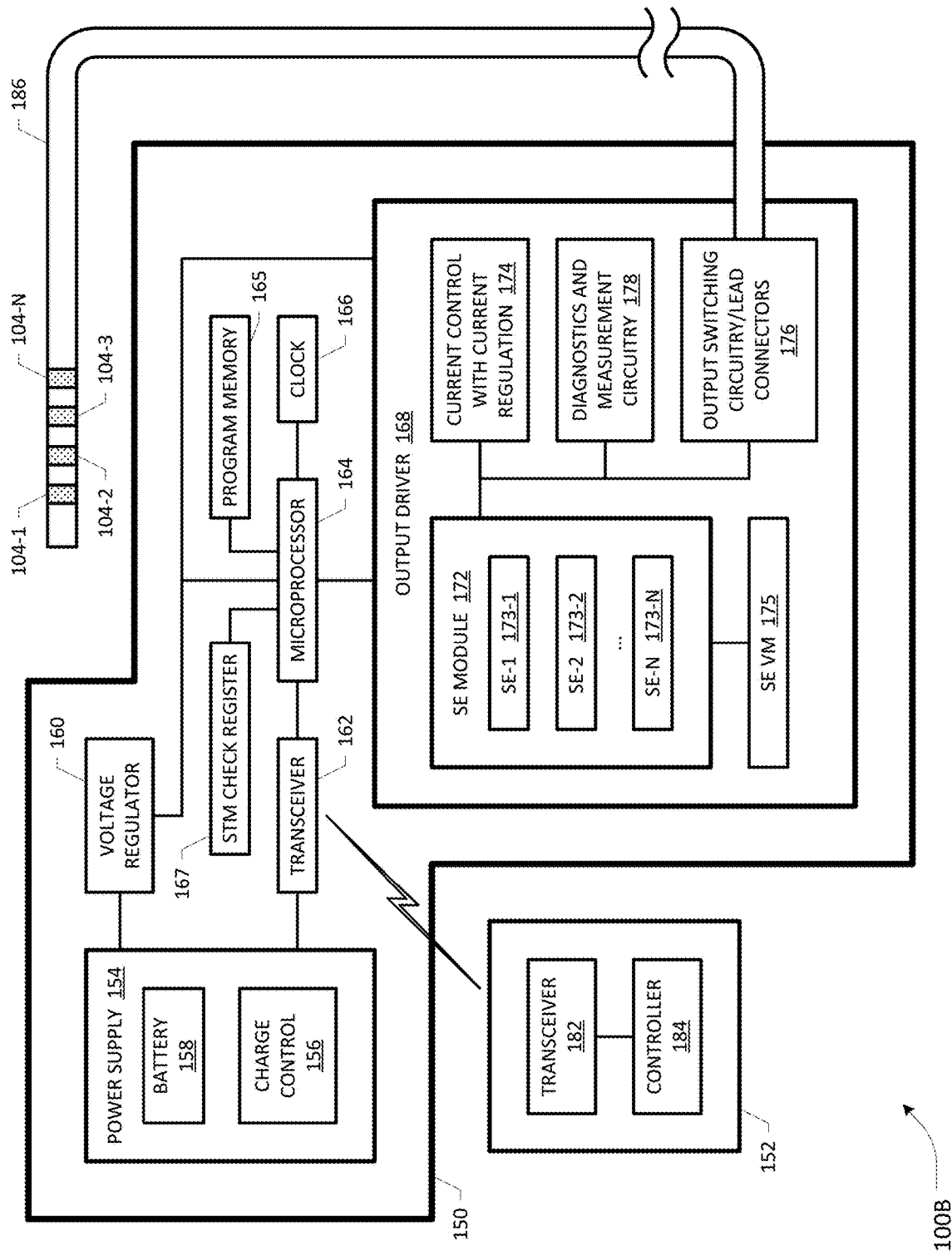
FIG. 1B depicts another view of a biostimulation system that illustrates additional details of an IMD's pulse generator including output driver circuitry wherein a switching matrix arrangement may be provided for facilitating STM functionality according to an embodiment of the present disclosure.

FIG. 1B depicts another view of a stimulation system 100B that illustrates additional details of an IMD's pulse generator including output driver circuitry wherein a switching matrix arrangement may be provided for facilitating STM functionality according to an embodiment of the present disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to external device 130 described in the foregoing sections. IPG 150 may be implanted within the body of a human or animal patient (not shown) for providing electrical stimulation from IPG 150 to a selected area of the body via lead 186 under control of external programmer/controller 152, wherein electrodes 104-1 to 104-N are electrically coupled to a corresponding plurality of output nodes (not specifically shown) driven by output switching circuitry and lead connector portion 176 of an output driver circuit 168. It should be appreciated that although lead 186 is illustrated to provide a stimulation portion of stimulation system 100B configured to provide stimulation remotely with respect to the generator portion 150 of stimulation system 100B, a lead as described herein is intended to encompass a variety of stimulation portion configurations including, e.g., a microstimulator electrode disposed adjacent to a generator portion.

In some arrangements, IPG 150 may be configured operate in STM while still in a sealed package in response to one or more mode selection control signals received from external controller 152 over a suitable wireless/M2M communication link, wherein respective switch circuit portions associated with one or more output nodes of the output switching circuitry 176 may be selectively tested with respect to switch integrity and current programmability as will be set forth hereinbelow.

Although example lead systems 186 and 106A/B shown in FIGS. 1A/1B are exemplified as a single implantable lead for effectuating therapy, discharge and testing operations, the teachings herein are not necessarily limited thereto. An example embodiment of the present disclosure may involve a lead system comprising two or more implantable leads, with each lead having a respective plurality of electrodes, wherein different combinations of electrodes/leads may be grouped into one or more channels in a stimulation therapy system. In some arrangements, stimulation current pulses according to different therapies may be applied by respective stimulation engines to different portions of electrodes based on a particular channel selection scheme regardless of whether one or more leads and/or one or more sets of electrodes are selected for stimulation. Accordingly, it will be appreciated that various portions of the output nodes driven by output switching circuitry 176 may be selected in myriad ways in an example embodiment when conducting test mode operations of IPG 150 while it is still in its package.

IPG 150 may be configured as a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, microcontroller (or microprocessor) 164, clock 166, and a program memory 165, which may be operated in concert for providing overall control of output driver circuitry 168. In one arrangement, output driver circuitry 168 may comprise a stimulation engine module (SEM) 172 having one or more stimulation engines (SEs) 173-1 to 173-N, each having respective current regulation circuitry and, optionally, switchable connectivity to a voltage multiplier (e.g., VM 175) as well as different combinations of output nodes via the output switching circuitry 176 according to the teachings herein. Alternatively or additionally, a separate current control/regulation block 174 along with a switchable voltage multiplier may be provided in some embodiments for operation with SEM 172. Further, suitable diagnostic circuitry 178 including measurement circuitry for measuring appropriate electrical characteristics of one or more output nodes and associated switching elements may also be provided as part of output driver 168 according to the teachings herein.

Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide recharging management with respect to battery 158. Transceiver 162 of an example embodiment of IPG 150 is operative to provide data/control communication between microprocessor 164 and a controller 184 of external programmer/controller 152, via transceiver 182 provided therewith. Transceiver 162 of an example embodiment, in addition to or in the alternative to providing data/control communications over an M2M communication protocol, may provide a conduit for delivering energy to power supply 158, e.g., via RF or inductive recharging as previously noted.

Microprocessor/controller 164 provides overall control with respect to the operation of IPG 150, such as in accordance with one or more programs stored in memory 165 or provided thereto by external programmer/controller 152. One or more SEs 173-1 to 173-N of module 172 may be configured to generate and deliver stimulation therapies having suitable pulse characteristics to selected sets or portions of electrodes 104-1 to 104-N under control of microcontroller 164. In general operation involving TDM functionality, for example, different SEs 173-1 to 173-N of MSE module 172 may be controlled to output optimized stimulation therapies (e.g., simultaneously or separately) to different sets of electrodes selected under programmatic control. By way of illustration, a stimulation therapy may comprise delivering a constant current pulse of a desired magnitude/amplitude, duration, phase, and frequency to a tissue load present with respect to particular ones/sets of electrodes 104-1 to 104-N, which may be represented as respective lumped-element electrode/tissue interface (ETI) loads. Clock circuitry 166 preferably provides system timing information, such as may be used by microcontroller 164 in controlling system operation, as well as for coordinating select engines of SEM 172 and/or VM 175 in generating desired voltages. Additionally, clock circuitry 166 may be configured to generate timing signals for controlling switchable connectivity with respect to one or more output nodes via output switching circuitry 176 in combination with one or more digital control signals generated by one or more combinational logic blocks depending on whether STM or TDM functionalities. An STM check register 167 may be provided in some embodiments for ensuring that test mode programming may be effectuated only intentionally, e.g., responsive to receiving appropriate mode selection control signals from external device 152.

In one example embodiment of IPG 150, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to provide a regulated supply $V_{OUT}$ within a range acceptable to circuitry of IPG 150, including output driver circuitry 168 having SE module 172, associated voltage multiplier 175 and/or current control and current regulation 174 for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too close to or below the $V_{OUT}$, causing the voltage regulator output voltage to also fall. In such a situation, therefore, the regulator can no longer provide the desired regulated output voltage. However, voltage regulator 160 of an embodiment may be adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control in association with suitable control signaling. For example, measurement or sensing circuitry, such as may utilize an analog-to-digital converter (ADC) in making voltage measurements may be utilized according to an embodiment to provide information with respect to the battery voltage, which may be used by a digital control system (e.g., supported by microcontroller 164) in order to provide appropriate control signals e.g., select signals, for controlling the output voltage of voltage regulator 160. Additional details regarding voltage regulation may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), which is hereby incorporated herein by reference.

Skilled artisans will recognize that although an embodiment of voltage regulation is set forth hereinabove, a variety of techniques and circuits may be provided for operation with an IPG having one or more SEs described herein in a particular implementation. As such, any suitable voltage regulator/multiplier arrangement may be adapted to provide a dynamic voltage adjustment to cover the voltage levels required for different test or stimulation currents under different test loads (e.g., resistances of output switch elements when turned on in STM operations) or tissue loads (after implanting the IMD in a patient) according to some example embodiments of the present disclosure.

Figure 2:
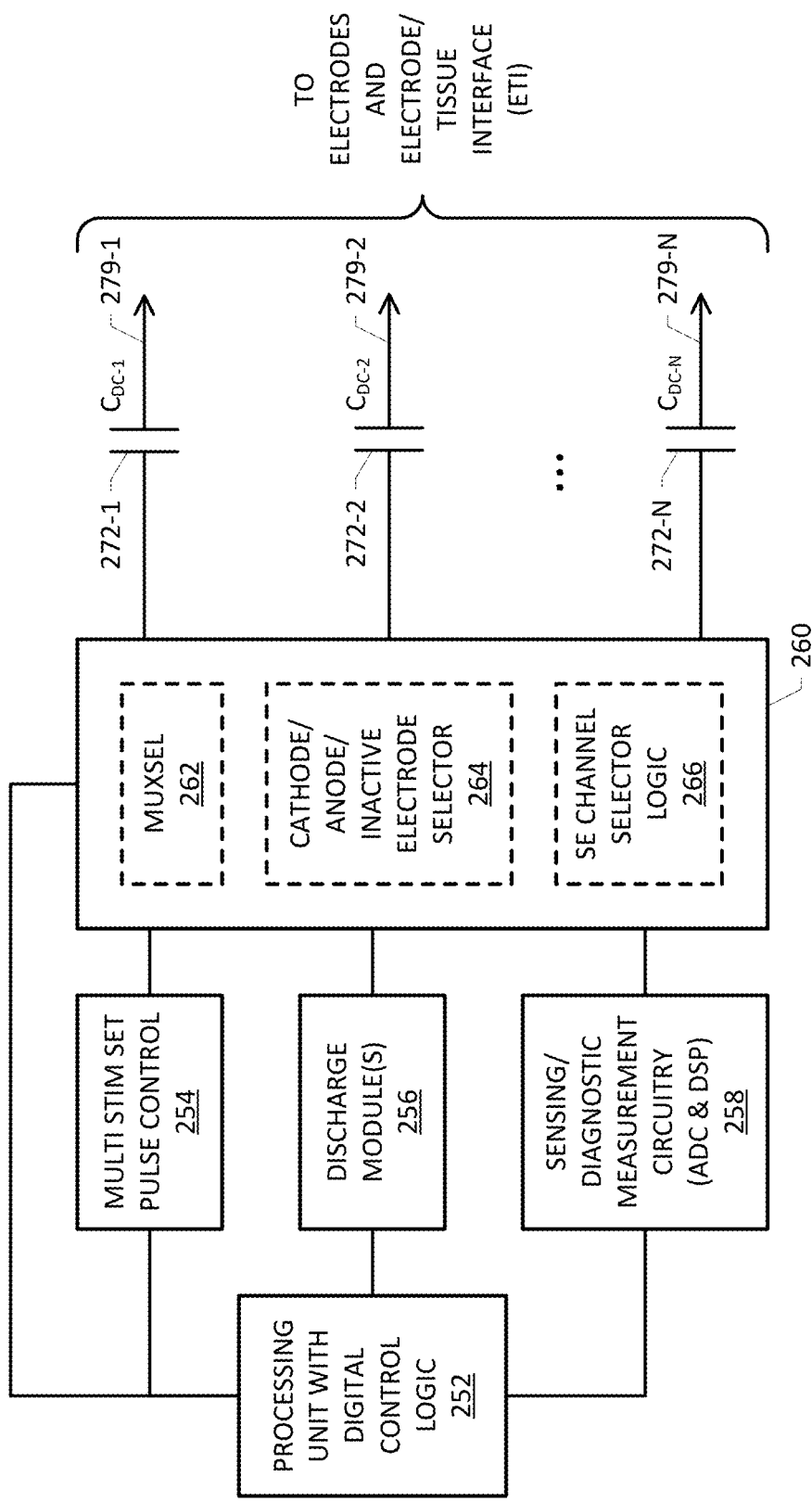
FIG. 2 depicts a block diagram of a pulse generator portion having stimulation engine selection control and associated diagnostic and measurement circuitry for purposes of an embodiment of the present disclosure.

FIG. 2 depicts a block diagram of a pulse generator portion 200 having stimulation engine selection control and associated diagnostic and measurement circuitry for purposes of an embodiment of the present disclosure. One skilled in the art will recognize upon reference hereto that various functionalities associated with example blocks shown as part of the pulse generator portion 200 may be distributed and/or integrated among one or more blocks, subsystems and/or modules described hereinabove with respect to FIGS. 1A/1B. Consistent with the description provided previously, a processing unit 252 having or associated with suitable digital control logic is operatively coupled to SE pulse control module 254, one or more discharge modules 256 and sensing/diagnostics and measurement circuitry 258 for facilitating various functionalities including but not limited to voltage measurements, active/passive discharge cycling, output node and/or electrode selection and configuration, SE selection, etc. under appropriate programmatic/diagnostics control. An input/output (I/O) interface block 260 having a plurality of output nodes (not specifically shown in this FIG.) may be operatively coupled to a plurality of lead connectors 279-1 to 279-N interfaced with respective electrodes, which interfaces may be modeled as suitable lumped-element ETI circuit representations, wherein the lead connectors and associated electrodes may be configured as one or more leads, each having a respective set/subset of electrodes. Regardless of the number of leads, a lead connector 279-1 to 279-N may be provided with a DC blocking stimulation capacitor ($C_{DC}$) for facilitating direct current flow blocking functionality with respect to the corresponding electrode that may be configured to operate as a stimulation node. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC-1}$ 272-1 is coupled to lead connector 279-1. Likewise, remaining lead connectors 279-N may be provided with respective $C_{DC-N}$ 272-N to facilitate DC blocking with respect to each corresponding lead electrode thereof.

Interface block 260 may include appropriate multiplexing and selection logic circuitry 262 and anode/cathode/inactive electrode selection logic circuitry 264 for facilitating measurement and sensing/diagnostics operations in accordance with STM and/or TDM functionalities wherein different output nodes (or, respective electrodes when implanted) associated with an electrode grouping of the lead system may be selectively configured for stimulation (e.g., anodic or cathodic stimulation), sensing, or designating unused/inactive states, etc., with appropriate electrical connections being made within an IPG device accordingly relative to the various components therein. In some embodiments, portions of diagnostic circuitry 258 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Additional details regarding configuring lead electrodes as cathodes or anodes, either during stimulation or for discharging, may be found in may be found in the '643 patent application publication incorporated by reference hereinabove. In a further arrangement involving multiple SEs, an SE selection block 266 may be provided for selectively coupling a (sub)set or portion of lead connectors (or corresponding output nodes) to a select one of the plurality of SEs under programmatic control, which selection may be mediated via an external programmer (e.g., a clinician programmer, a technician controller, etc.) as previously noted.

Figure 3:
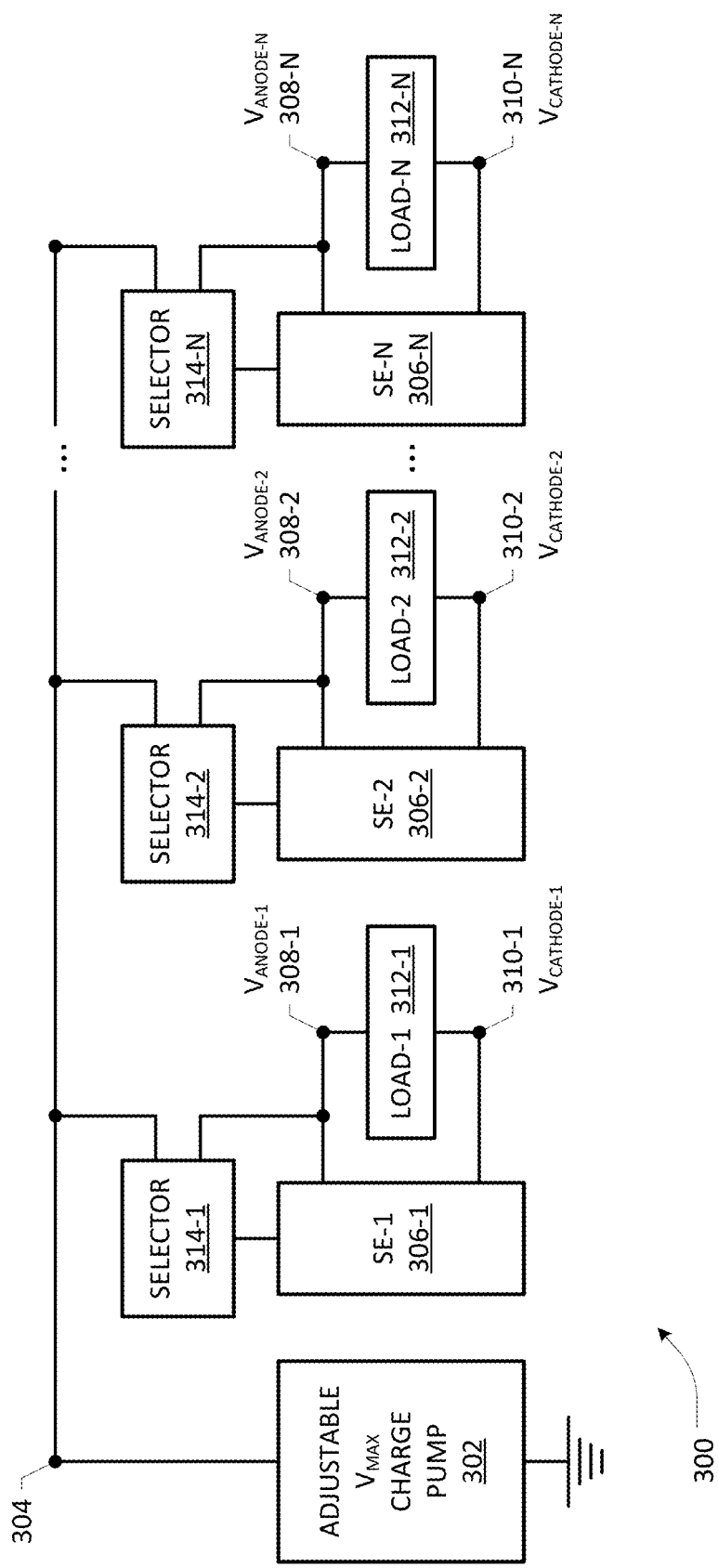
FIG. 3 depicts an example circuit arrangement including multiple stimulation engines that may be switchably connectable to different sets of electrodes depending on output switch selection and STM control according to an embodiment of the present disclosure.

FIG. 3 depicts an example circuit arrangement 300 having multiple SEs that may be switchably connectable to a common voltage multiplier for driving different output nodes depending on electrode/output node selection and mode selection control according to an embodiment of the present disclosure. An adjustable voltage multiplier (VMULT or VM) 302 may be configured as a charge pump arrangement that can step up or step down from a regulated voltage supply, e.g., from a battery, to provide an output voltage that can cover up to a certain maximum voltage level ($V_{MAX}$) in order to support a sufficient voltage headroom (e.g., 12.0V to 20.0V) for different voltage settings applicable for a therapy application or for a testing scenario. For example, a DRG application may require a lower $V_{MAX}$ level than an SCS or DBS application. In one arrangement, VMULT 302 may be implemented as a stacked charge pump capacitor arrangement to provide different output voltages at VM node 304. In one arrangement, VMULT 302 may be configured to operate as a voltage supply that may be commonly used by different SEs 306-1 to 306-N to apply stimulation to respective sets of electrodes of an implanted lead system, wherein a charge pump arrangement including a plurality of pump and storage capacitors may be interconnected under suitable digital control to provide variable target output voltages ($V_{TARG}$). Additional details regarding such an arrangement may be found in U.S. Pat. No. 8,446,212, entitled "PULSE GENERATOR HAVING AN EFFICIENT FRACTIONAL VOLTAGE CONVERTER AND METHOD OF USE", which is incorporated herein by reference.

When STM is invoked (e.g., while the IMD is in a sealed package), a particular SE may be selectively coupled to a selected output node via associated output switch element portion to test the integrity of the switching operations, switch elements impedances, pulse current programmability, etc. In an implanted state, a plurality of loads 312-1 to 312-N, each representing a respective set of electrodes, may be coupled between an anodic node ($V_{ANODE}$) and a cathodic node ($V_{CATHODE}$) of a respective SE operative to stimulate the tissue. In some embodiments, each SE may be provided with a selector/switching module for selectively coupling and/or energizing a select set or portion of the electrodes as the respective load therefor. As shown in FIG. 3, selector modules 314-1 to 314-N are operative with respect to corresponding SE modules 306-1 to 306-N. In some embodiments, the overall SE selection switching and associated logic functionality may be centrally or commonly provided with respect to all SE modules 306-1 to 306-N as part of an IMD's output switching circuitry I/O interface block. Also, one or more additional switching elements may be provided (e.g., one switching element per output node or electrode) as part of the IMD's output switching circuitry that may be configured to effectuate switchable connectivity between VM node 304 and output nodes for facilitating STM operations, wherein an internal circuit path may be formed in combination with a selected SE. Such internal circuit paths may be advantageously utilized in creating one or more measurement loops between VM node 304 and the selected SE's ground/reference for measurement purposes while there is no connectivity to the lead system (e.g., in the sealed package condition). As will be seen further below, the additional switch elements may also be activated or actuated (i.e., turned on or off) in TDM operations after implanting the IMD for effectuating therapy and discharge operations. Accordingly, the additional switching elements may be referred to as "dual mode" (DM) elements whereas the switching elements for selectively coupling SEs to output nodes may be referred to as stimulation engine selection (SES) elements. Regardless of how the SE selection and/or electrode/output node set selection is configured in an example embodiment, suitable digital control logic may be implemented to generate appropriate control signals for controlling/managing switchable connectivity with respect to SE selection and output node connectivity in order to effectuate STM and TDM operations in an IMD according to the teachings herein.

Figure 4:
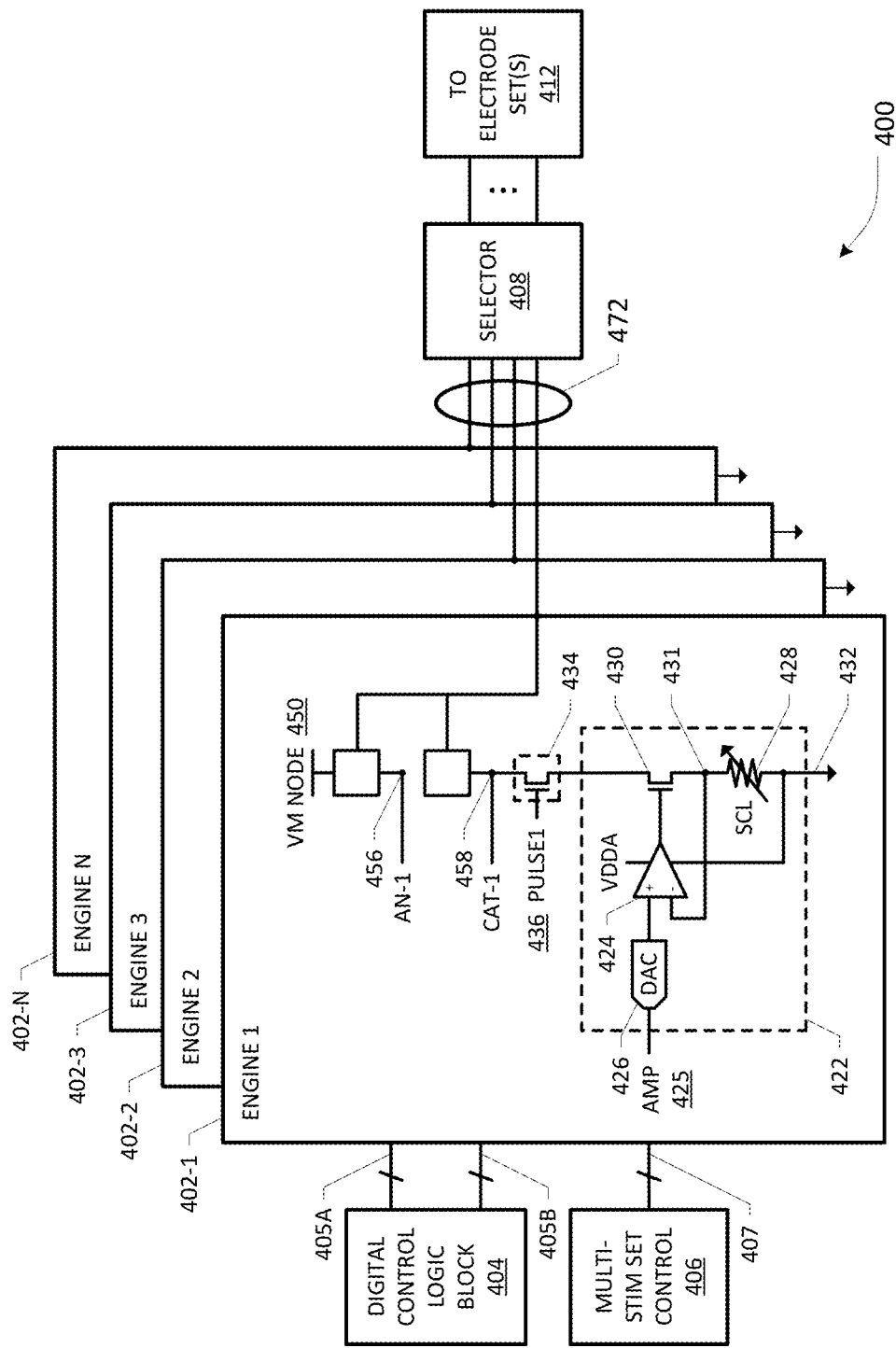
FIG. 4 depicts an example circuit arrangement with additional details of one or more stimulation engines that may be switchably connected via output switching circuitry that includes dual mode (DM) switches and stimulation engine selection (SES) switches for facilitating STM functionality and electrode discharge functionality depending on output switch selection and STM control according to an embodiment of the present disclosure.

FIG. 4 depicts an example circuit arrangement with additional details of one or more stimulation engines that may be switchably connected via output switching circuitry that includes a plurality of DM switches and a plurality of SES switches for facilitating STM operations and TDM operations including electrode discharge functionality depending on output switch selection and STM control according to an embodiment of the present disclosure. In one implementation, circuit arrangement 400 may include multiple SE instances for purposes of the present disclosure consistent with the foregoing arrangement of FIG. 3. A plurality of stimulation engines 402-1 to 402-N may be controlled by a digital control logic block 404 and a multi-stim set control block 406 that may be provided in conjunction with or as part of an IMD architecture as discussed above, wherein engines 402-1 to 402-N are substantially analogous to SE modules 306-1 to 306-N of FIG. 3. In one embodiment, each stimulation engine includes a programmable current regulator operative as a current sink circuit and switching circuitry configured to actuate a switchable coupling between the current sink circuit and a cathodic node of the stimulation engine. Output switching circuitry 408 disposed between SEs 402-1 to 402-N and a plurality of output nodes (and corresponding electrodes, by extension) comprises respective pluralities of DM switches (corresponding to the number of output nodes) and SES switches (corresponding to the number of SE instances for each output node), wherein an output node or electrode (or a set thereof) may be switchably connected via a DM switch to a voltage multiplier (VM) node, e.g., VM node 450, operating to drive an anodic node of an SE, or via an SES switch to a cathodic node of an SE. In one arrangement, digital control logic block 404, which may be implemented as a state machine or any type of combinational logic, and output switching circuitry 408 are operative under appropriate timing control for independently controlling respective stimulation engines 402-1 to 402-N such that each engine may be activated to energize a corresponding set of output nodes or electrodes independently from or in concert with the remaining stimulation engines based on applicable test or stimulation settings provided to the respective engines 402-1 to 402-N under multi-stim set control 406. As previously noted, multiple output nodes corresponding electrode sets 412 of an IMD may be mapped to different output channels, which may be driven by respective stimulation engines depending how the DM and SES elements may be configured (e.g., actuated to be in on or off states) under suitable digital control logic signals.

By way of example, an anodic node 456 of stimulation engine 402-1 may be coupled to VMULT/VM node 450 (e.g., driven by a common VM output node such as node 304 in FIG. 3) via a DM switch connection path traversing through output switching circuitry 408. A cathodic node 458 of SE 402-1 is switchably connectable via switching element 434 to a programmable current sink 422. A select output node may be selectively coupled to VM node 450 via DM switch connectivity or to cathodic node 458 via SES switch connectivity provided in output switching circuitry 408 depending on mode selection and output node polarity (e.g., configured as an anode or a cathode). Reference numeral 472 refers to the plurality of DM and SES switch connection paths between multiple SEs and output switching circuitry 408. Although not specifically shown in this FIG., it should be appreciated that switching elements operative as DM and SES switches of output switching circuitry 408 may be implemented using a variety of electronic devices such as transistors, diodes, gates, etc., that may be actuated responsive to appropriately timed digital control signals having suitable logic levels depending on whether STM or TDM operations are effectuated with respect to a select one or subset of the output nodes (e.g., for activating an internal circuit path with respect to a particular output node selected for testing or energizing a pair/set of electrodes in order to stimulate tissue or cause a discharge therefrom, etc.).

In one example implementation, current sink circuit 422 of example engine 402-1 may include a digital-to-analog converter (DAC) 426 interfacing with appropriate pulse voltage control signal 425 (e.g., having suitable magnitude and polarity depending on the type of stimulation current being programmed) to generate a digitally-programmed analog voltage level as an output signal that may be provided to an error amplifier 424. In one arrangement, error amplifier 424 may be implemented as an op amp having two inputs for providing a differential input and operative with a power supply rail voltage VDDA and ground 432 that may be commonly tied to an IMD battery ground along with other ground nodes of remaining stimulation engines. Accordingly, the digitally-programmed analog voltage signal (VDAC) output may be coupled to a first input of error amplifier 424, wherein a second input is coupled to a programmable resistor network 428 operative to provide a digitally-programmed resistance (RSCALE) in a feedback loop arrangement for modulating a current sink output. In general operation, error amplifier 424 may be programmatically configured to generate a desired amount of stimulation current ($I_{STIM}$), which may be set by the application of Ohm's Law in view of the digitally-programmed resistance RSCALE, where $I_{STIM}$=(VDAC/RSCALE), at a node 431 to which the programmable resistor network 428 is connected. A current conducting device 430 actuated by the output of error amplifier 424 may be coupled to node 431 for facilitating the stimulation current $I_{STIM}$ flowing through one or more electrodes (i.e., a particular electrode set) when the select stimulation engine, e.g., engine 402-1, is in stimulation mode wherein cathodic node 458 of the select stimulation engine is connected to one side of the selected electrode set and anodic node 456 of the select stimulation engine coupled to the associated electrodes across the ETI interface is connected to the VM output connection node 450 under suitable control signal logic.

In one embodiment, the digital control logic block 404 may comprise combinational circuitry to generate a plurality of pulse control signals 405A/405B for respectively actuating at least a subset of stimulation engines 402-1 to 402-N by generating suitable signals (e.g., PULSE1 436) to turn on or off switching element 434 of the respective stimulation engine depending on whether the stimulation engine is operating in stimulation mode or discharge mode. Further, timing control of switching circuitry 434 of each respective stimulation engine may be coordinated with the timing of pulse voltage control signals 425 (designated as AMP signals) provided to respective current sink circuitry 422 for achieving synchronized operations of the respective stimulation engine. It should be appreciated that digital control logic block 404 and multi-stim set control block 406 may therefore be configured to provide appropriate switch control and SE control signals 405A/405B and pulse setting signals 407 that are coordinated for respective stimulation engines. In some arrangements, such switch and SE control signals 405A/405B and pulse setting signals 407 may be different for different stimulation engines in terms of logic levels, timing control, amplitude/range levels, and the like, so that each stimulation engine's operations for stimulation and/or discharge of associated electrode sets may be independently controlled. Accordingly, in such a scenario, a portion of stimulation engines may be activated for stimulating corresponding sets of electrodes, another portion of stimulation engines may be disposed in a discharge mode for discharging the electrode sets that may have been previously energized by such stimulation engines, while a yet another portion of stimulation engines may not be connected to any electrodes at all (i.e., in inactive or off state).

Figure 5:
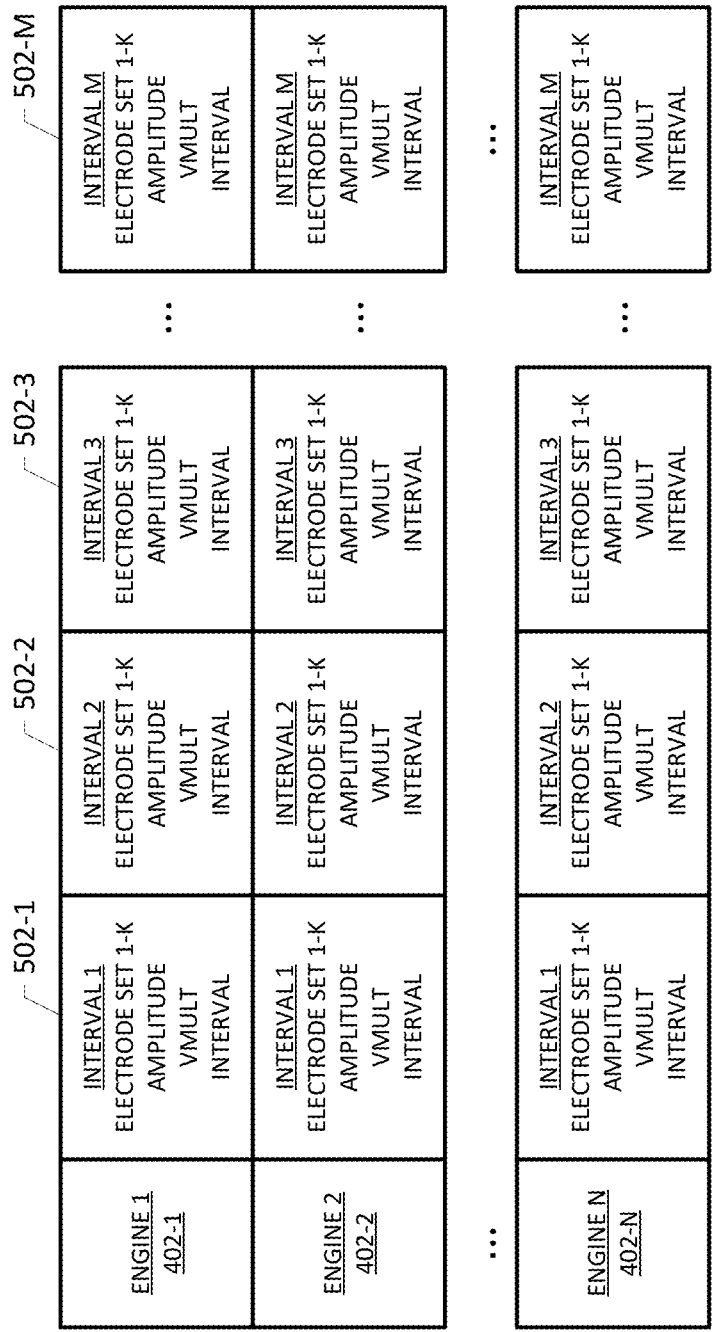
FIGS. 5 and 6 depict example test stimulation settings and combinations of output nodes corresponding to respective electrodes for selectively testing different switching circuit portions of the output switching circuitry in an illustrative scenario according to an implementation of the present patent disclosure.
Figure 6:
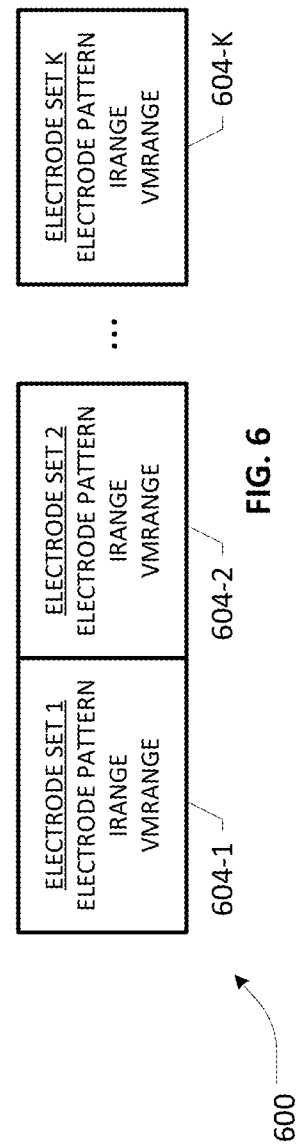

FIGS. 5 and 6 depict example test or stimulation settings and one or more combinations of electrode/output node sets with respect to different stimulation engines in an illustrative scenario according to an implementation of the present patent disclosure. Table 500 of FIG. 5 illustrates engines 402-1 to 402-N, each configurable to provide different settings 502-1 to 502-M over a plurality of time intervals, either for providing stimulation via select ETI loads or for testing a select one or more output nodes via internal circuit paths caused in an IMD's output switching circuitry. Each setting may correspond to a particular electrode set (e.g., sets 1 to K, each comprising a particular combination selected from the total number of electrodes of a lead system), pulse amplitude, VM voltage level as well as a corresponding time duration, among others. It should be noted that different stimulation engines may have different stimulation and/or test settings in respect of any of the parameters thereof. Table 600 of FIG. 6 is illustrative of different output node selections or electrode patterns and associated electrical parametric ranges, collectively referred to by reference numerals 604-1 to 604-K, corresponding to respective electrode/output node sets (K).

Additional embodiments of example stimulation engines that may be configured to operate in conjunction with output switching circuitry having STM capability may be found in one or more of the following: (i) U.S. patent application Ser. No. 16/790,443, filed Feb. 13, 2020, published on Aug. 19, 2021 as Publication No. US 2021-0252291 A1, entitled, "NEUROMODULATION THERAPY WITH A MULTIPLE STIMULATION ENGINE SYSTEM"; and (ii) U.S. patent application Ser. No. 16/778,255, filed Jan. 31, 2020, issued on Oct. 5, 2021 as U.S. Pat. No. 11,135,431, entitled, "IMPLANTABLE PULSE GENERATOR WITH MULTIPLE STIMULATION ENGINES"; each of which is incorporated herein by reference.

Figure 7:
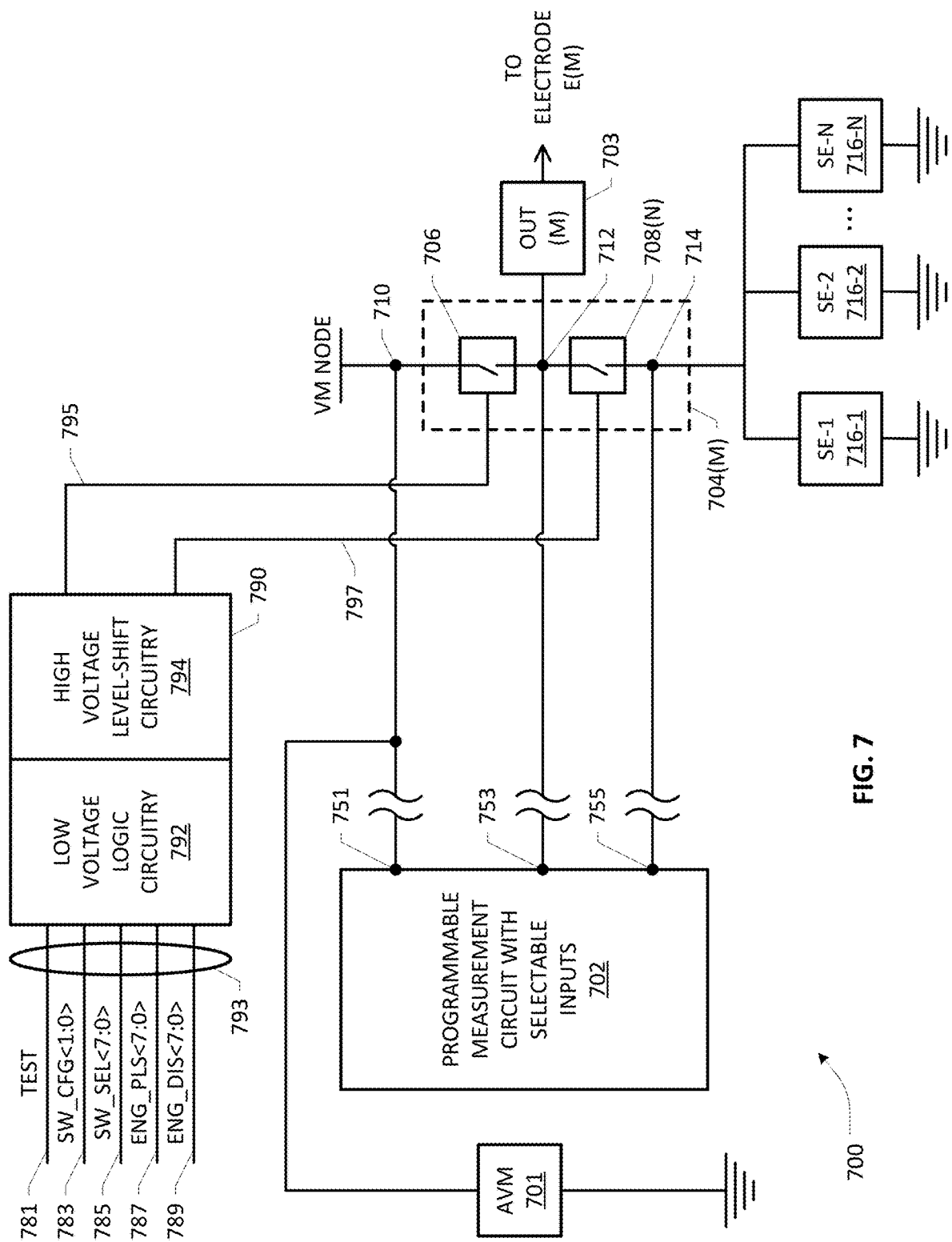
FIG. 7 illustrates a block diagram of a circuit arrangement wherein an example output switching circuit having a plurality of output switching portions corresponding to a plurality of output nodes according to an embodiment of the present disclosure.

FIG. 7 illustrates a block diagram of a circuit arrangement wherein an example output switching circuit having a plurality of output switching portions that may be selectively coupled to a programmable measurement circuit for testing different combinations of output nodes and one or more SEs of an IMD in a packaged condition according to an embodiment of the present disclosure. In one embodiment, circuit arrangement 700 may include a plurality of output switching portions 704(M), each operating to drive a respective one of a plurality of output nodes 703(M), which may be electrically coupled to a corresponding plurality of electrodes of one or more leads when the IMD is deployed in an implanted state. Each output switching portion 704(M) includes a dual mode (DM) switch 706 (operative to couple a select output node to a voltage multiplier output node) and a plurality of stimulation engine selection (SES) switches 708(N) (also referred to as cathode selection (CS) switches) that may be selectively activated to couple a select output node to a cathodic node of a particular one of a corresponding plurality of SEs 716-1 to 716-N provided in the IMD. Output switching portions 704(M) including DM switches 706 and SES switches 708(N) may be formed as a switching matrix of the IMD's output driver circuitry (e.g., output driver 168 shown in FIG. 1B), wherein different DM and SES switch combinations may be selectively activated to be turned on (i.e., closed state) or off (i.e., open state) depending on the logic states of respective switch control signals that may be generated responsive to a plurality of digital control signals 793 selectively asserted depending on whether STM or TDM functionalities of the IMD are invoked. In one arrangement, one or more combinational logic blocks 790 may be operative in response to at least a portion of the following control signals: TEST signal 781 (operating to turn on, select or otherwise effectuate STM functionality, which may be generated in response to a mode selection control signal received from an external device as previously noted); SW_CFG[1:0] signals 783 (operating to configure an output node switch as an anode, a cathode or in a open state (i.e., high impedance state); SW_SEL[(N−1):0] signals 785 (operating to select which SE is to be electrically coupled to a select output node at the SE's cathodic node); ENG_PLS [(N−1):0] signals 787 (operating to provide stimulation pulse timing); and ENG_DIS[(N−1):0] signals 789 (operating to provide discharge pulse timing). Skilled artisans will recognize that additional digital control signals may also be provided in some arrangements depending on how the SEs are configured (e.g., operating with individual/variable anodic voltage levels and/or having individual current sources in addition to current sinks as set forth in some example embodiments), selection of different combinations of multiple sets of output nodes, and the like. In one arrangement, digital control signals 793 may be generated in a low voltage domain of the IMD circuitry, thereby requiring a level-shifting circuit block to generate, provide or otherwise obtain output switch control signals having suitable high voltage levels. Accordingly, logic block 790 may include low voltage logic level circuitry 792 operating in combination with level shift circuitry 794 for generating DM switch control signals 795 and SES switch control signals 797 with respect to each output switch portion 704(M). It will be recognized that the various blocks of combinational logic circuitry set forth herein may be implemented in a number of ways depending on design considerations, e.g., using programmable logic devices, gate arrays, half adders, full adders, multiplexers, demultiplexers, encoders and decoders, state machines, programmable logic arrays, programmable array logic circuits involving combinations of digital logic gates such as AND/NAND gates, OR/NOR gates, etc.

A programmable measurement circuit 702 having selectable inputs may be coupled at various nodes of each output switching portion 704(M) for effectuating a measurement path across different portions of the switching circuitry depending on implementation and measurement selection. As illustrated, a first input 751 of the measurement circuit 702 may be coupled to a voltage output (VM) node 710 driven by an adjustable voltage multiplier (AVM) 701, wherein VM node 710 may be coupled to any select output node 703(M) depending on the state of the corresponding DM switch 706. A second input 753 of the measurement circuit 702 may be coupled to an internal impedance divider node 712 coupled to drive the select output node 703(M) and a third input 755 of the measurement circuit 702 may be selectively coupled to cathode 714 of a select SE that may be coupled to any select output node 703(M) depending on the state of the corresponding SES switch 708(N). In one arrangement, the measurement circuit 702 may be provided as part of the IMD's sensing/diagnostic circuitry operating under programmatic control, e.g., circuitry 258 of FIG. 2 described above.

Figure 8:
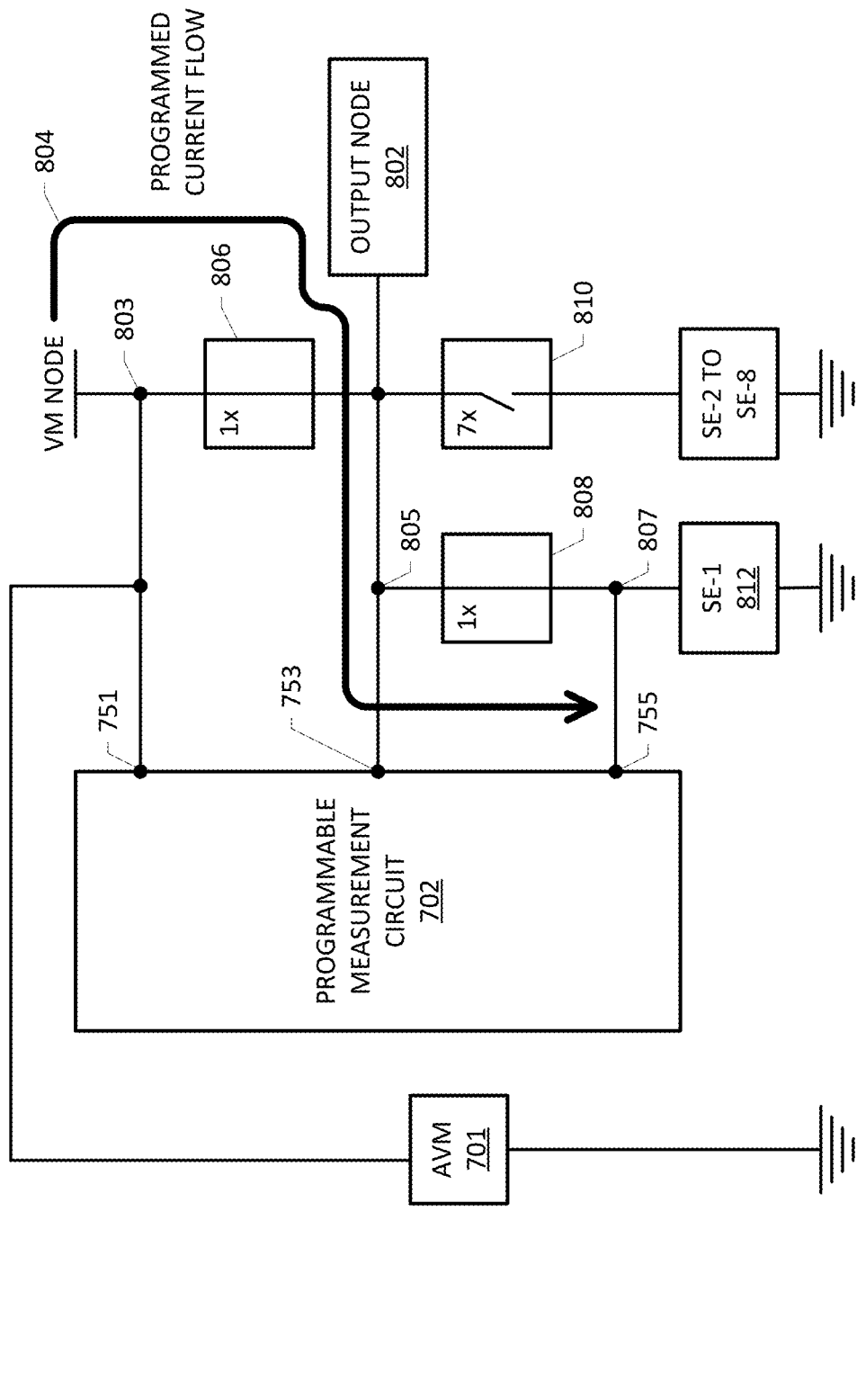
FIG. 8 depicts another view of the circuit arrangement of FIG. 7 wherein an internal circuit path associated with a particular output node may be effectuated via the output switching circuitry for measurement purposes according to an embodiment of the present disclosure.

FIG. 8 depicts another view of the circuit arrangement of FIG. 7 wherein an internal circuit path associated with a particular output node of an IMD may be effectuated via the output switching circuitry for measurement purposes with respect to testing the integrity and other electrical characteristics of the switching circuit portion corresponding to the particular output node according to an embodiment of the present disclosure. By asserting TEST, SW_CFG and SW_SEL control signals appropriately, a particular output node, e.g., output node 802, is selected to be connected to VM node 710 via a closed DM switch 806. Output node 802 is also connected to a cathode 807 of selected SE-1 812 via a closed SES switch 808. Remaining SES switches 810 corresponding to seven other SEs in the example embodiment involving eight SEs are turned off. Because DM switch 806 and SES switch 808 are in a series connection when both switches are closed, an internal circuit path 804 may be established for conducting a programmable current through the select SE 812. Further, the internal circuit path 804 may be selectively connected to the inputs of measurement circuit 702 at different "tapping" points, thereby effectuating different measurement loops for testing the DM and SES switch functionality separately or in combination in order to verify switch operation, switch impedance and current programmability. For example, a measurement loop may be formed by coupling VM node 803 to measurement input 751 and coupling internal node 805 of the switching circuit portion associated with output node 802 to input 753 of the measurement circuit 702 for measuring the integrity/impedance of DM switch 806. Likewise, another measurement loop may be formed by coupling internal node 805 of the switching circuit portion associated with output node 802 to measurement input 753 and coupling cathodic node 807 to input 755 of the measurement circuit 702 for measuring the integrity/impedance of SES switch 806. Yet another measurement loop may be formed by coupling VM node 710 to measurement input 751 and coupling cathodic node 807 to input 755 of the measurement circuit 702 for verifying the overall integrity of the internal circuit path 804.

Figure 9:
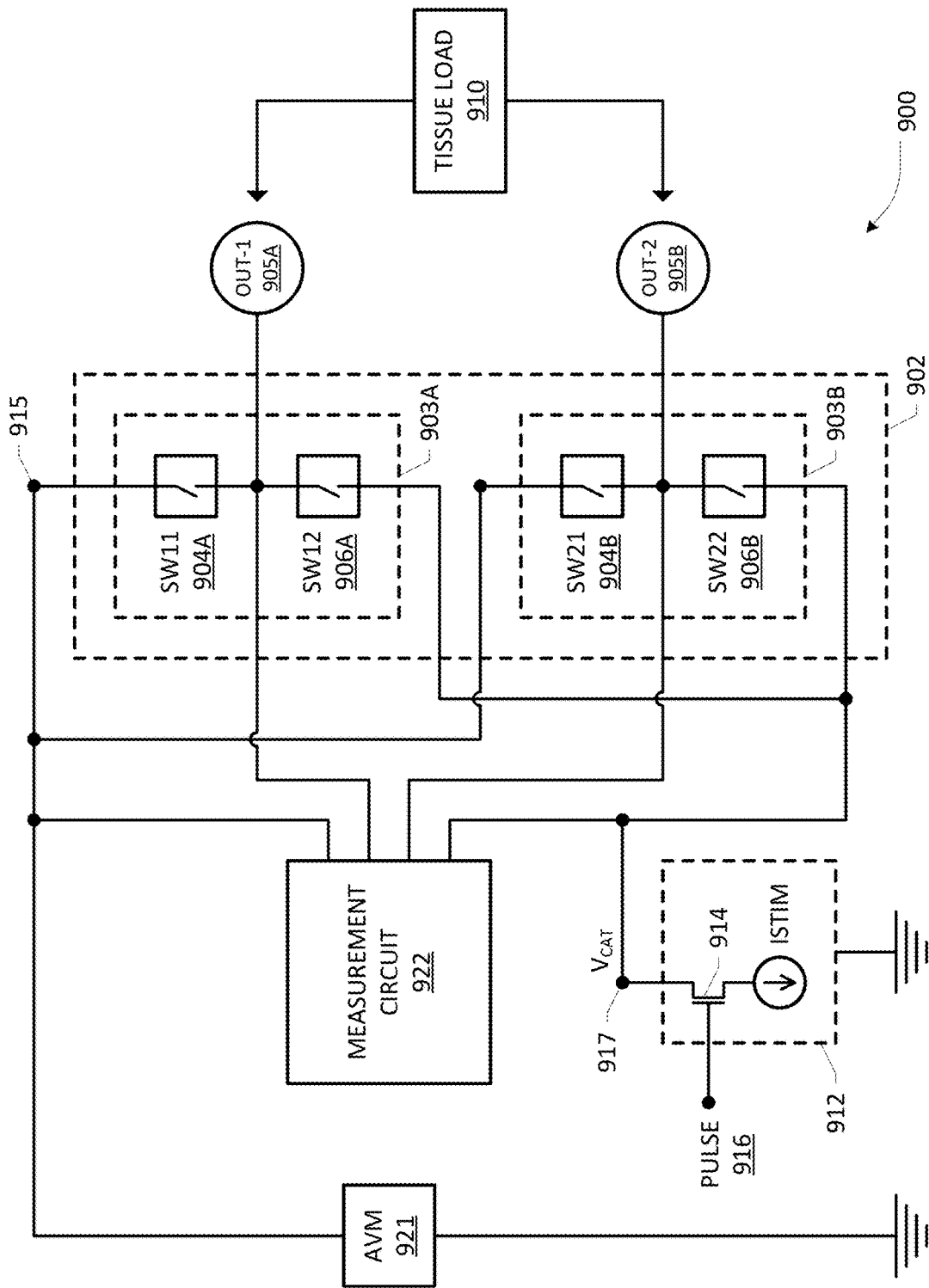
FIG. 9 depicts an example output switching circuitry for a two-electrode arrangement wherein STM functionality as well as stimulation and discharge modes may be implemented in an IMD according to an embodiment of the present disclosure.

FIG. 9 depicts an example output switching circuit for a two-electrode arrangement wherein STM functionality as well as stimulation and discharge modes may be implemented in an IMD according to an embodiment of the present disclosure. As illustrated, circuit arrangement 900 includes an output switching circuit 902 including an output switching portion 903A associated with output node 905A and an output switching portion 903B associated with output node 905B. Output nodes 905A/905B may be coupled to respective electrodes or (sets of electrodes) for facilitating stimulation therapy and discharge operations with respect to a tissue load 910 when implanted within a patient. However, as there is no external load connectivity to output nodes 905A/905B when the IMD is in a sealed package condition, output switching portions 903A/903B may be configured to effectuate two internal circuit paths corresponding to the two output nodes, thereby facilitating appropriate tests and measurements under STM functionality as set forth above.

By way of illustration, a single SE 912 operating responsive to a PULSE signal 916 exemplified for coupling to drive a cathode (VCAT) 917 thereof. Output switching portion 903A associated with output node 905A includes SW11 904A operating as a DM switch and SW12 906A operating as an SES switch. Likewise, output switching portion 903B associated with output node 905B includes SW21 904B operating as a DM switch and SW22 906B operating as an SES switch. Circuit arrangement 900 may include a measurement circuit 922 having selectable inputs that may be coupled at different tapping points with respect to each output switching portion in order to effectuate appropriate measurement loops, wherein AVM 921 is operative to drive a common VM node 915, as described above.

For testing the integrity of output switching portion 903A during STM, the associated output node 905A may be selected (e.g., configured as an anode) and the following logic states may be effectuated: S11 904A and S12 906A are turned on (i.e., closed) and S21 904B and S22 906B are turned off (i.e., open), while PULSE 916 is asserted high, thereby turning on switch 914. An internal circuit path comprising at least a series portion of closed switches S11 904A and S12 906A disposed between VM node 915 and VCAT 917 may therefore be formed for testing the integrity and impedances of closed switches S11 904A and S12 906A as well as the programmability of a first test stimulation current (ISTIM) by the measurement circuit 922. In similar fashion, the integrity of output switching portion 903B associated with output node 905B may be tested during STM by configuring it as an anode and effectuating the following logic states: S11 904A and S12 906A are turned off (i.e., open) and S21 904B and S22 906B are turned on (i.e., closed), while PULSE 916 is asserted high, thereby turning on switch 914. An internal circuit path associated with output node 905B thus comprises at least a series portion of closed switches S21 904B and S22 906B disposed between VM node 915 and VCAT 917, which facilitates the impedance measurements of closed switches S21 904B and S22 906B as well as the programmability of another test stimulation current (ISTIM) by the measurement circuit 922. Test currents for different measurement loops may be programmed to have a variety of pulse patterns, characteristics, parameters, etc., some of which may also be part of one or more stimulation settings that may be applied after the IMD is implanted for providing therapy.

During normal TDM operations after implanting the IMD in a patient, a stimulation mode may involve configuring an electrode coupled to output node 905A as an anode and an electrode coupled to output node 905B as a cathode for providing stimulation therapy pulses. In one example arrangement, such operations may be effectuated pursuant to disabling the TEST signal and asserting SW_CFG and SW_SEL control signals appropriately along with actuating an ENG_PLS signal (e.g., PULSE 916). Because output node 905A is configured as anode, S11 904A is turned on and S12 906A is turned off, whereby output node 905A is coupled to VM node 915. On the other hand, output node 905B is configured as cathode, coupled to VCAT 917 via S22 906B that is closed while S21 904B is turned off. A programmable stimulation pulse current to the tissue load 910 may be applied by appropriately asserting the ENG_PLS signal (e.g., PULSE 916 is driven to a logic high). In a discharge mode operation, ENG_PLS signal (e.g., PULSE 916) is deasserted (e.g., logic low) while the following switch logic is effectuated: both S11 904A and S21 904B are turned off and both S12 906A and S22 906B are turned on, which causes both output nodes 905A/905B to be connected to VCAT 917. In other words, during discharge, an output node previously configured as a cathode for stimulation operations remains as a cathode while an output node previously configured as an anode for stimulation operations is changed to a cathodic connection.

Although the output switch logic set forth above is exemplified in the context of STM and TDM operations involving a single SE coupled to a pair of output nodes/electrodes, it will be appreciated that the switch logic is expandable to any number of output nodes and SEs in any combination, mutatis mutandis.

Figures 10, 11:
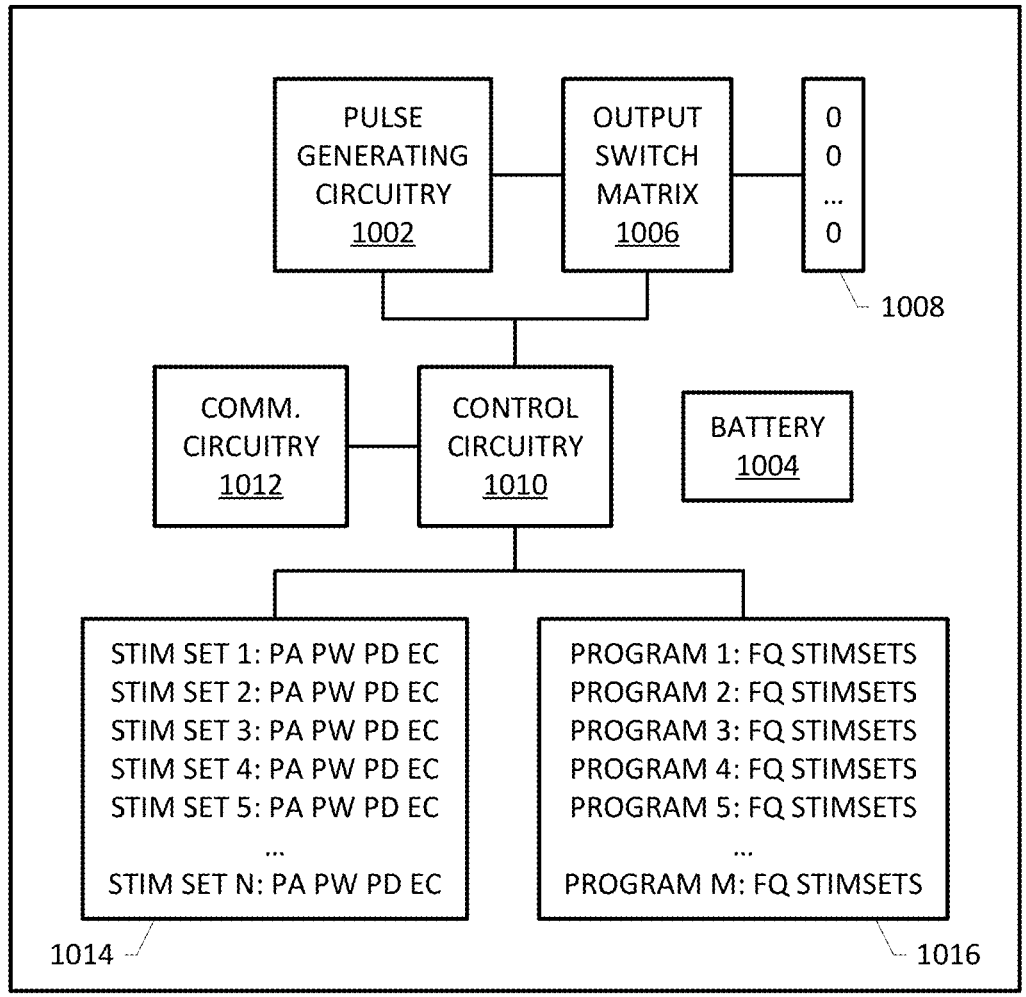
FIG. 10 depicts another view of an IMD having an output switch matrix configured to effectuate STM functionality for testing various stimulation settings and programs according to an embodiment of the present disclosure.
FIG. 11 depicts an example test program that may include different pulse settings and patterns including burst and/or tonic stimulation patterns according to one representative embodiment.

FIG. 10 depicts another view of an example IMD having an output switch matrix configured to effectuate STM functionality for testing various stimulation settings and programs according to an embodiment of the present disclosure. IMD 1000 may be programmed to test and/or deliver burst and tonic stimulation patterns in accordance with some representative embodiments. Similar to the embodiments set forth in other drawing Figures, IMD 1000 includes battery/power supply 1004, pulse generating circuitry 1002 (e.g., including one or more SE embodiments described above), output switch matrix 1006, control circuitry 1010, and communication circuitry 1012. Control circuitry 1010 controls the generation of pulses by pulse generating circuitry 1002 and the delivery of the generated pulses by output switch matrix 1006 that may be switchably configured to drive select output nodes 1008 in accordance with the teachings herein. In one arrangement, control circuitry 1010 controls the amplitude and pulse width of a respective pulse by controlling pulse generating circuitry 1002. Additionally, control circuitry 1010 controls the timing of the generation of pulses by controlling pulse generating circuitry 1002. Control circuitry 1010 further configures output switch matrix 1006 to control the polarity associated with a plurality of outputs 1008 associated with switch matrix 1006 depending on whether STM or TDM operations are invoked in accordance with the teachings herein. In one representative embodiment, control circuitry 1010 may be implemented using a microprocessor and suitable software instructions to implement the appropriate system control. Alternatively, control circuitry 1010 may comprise an application specific integrated circuit (ASIC). Regardless of how example control circuitry 1010 is implemented, a plurality of test/stimulation sets 1014 may be defined in a memory that may be selectively applied in a sequence by control circuitry 1010. Each test/stim set may define a pulse amplitude, a pulse width, a pulse delay, and an output/electrode selection (depending on whether STM operations or TDM operations are invoked). One or more test/stim sets may be combined as a test/stimulation program that may be executed depending on whether STM is selected while the IMD is in a sealed package or implanted in a patient. A plurality of stimulation programs 1016 are exemplified in the embodiment shown in FIG. 10. In one arrangement, a test or stimulation program may define a plurality of pulses to be generated in succession and the frequency of repetition of the pulses. In general, when control circuitry 1010 executes a test/stimulation program, control circuitry 1014 first retrieves the stimulation parameters for a first stimulation set of the stimulation program for modifying/adjusting an amplitude setting of pulse generating circuitry 1002 according to the amplitude parameter of the stim set. Control circuitry 1010 also configures output switch matrix 1006 according to the electrode/output node combination of the stim set. Control circuitry 1010 may further cause pulse generating circuitry 1002 to generate a pulse for an amount of time as defined by the pulse width parameter. In one arrangement, measurement circuitry (not shown in this FIG.) may be configured to measure appropriate output switching characteristics, which may be made available to communication circuitry 1012 for transmission to an external device. Control circuitry 1010 may be configured to stop the pulse generation and wait an amount of time equal to the pulse delay parameter specified in the test/stimulation set. There-after, control circuitry 1010 may proceed to a next stimulation set in the stimulation program and continue to repeat the process. In one arrangement, each test/stimulation set in a test/stimulation program may be executed in the same manner unless additional control signals are received (e.g., generated responsive to user input).

Depending on implementation, example test/stimulation programs may comprise programs operative in a variety of therapy applications including but not limited SCS therapy, DBS therapy, DRG therapy, cochlear stimulation therapy, drug delivery therapy, cardiac pacemaker therapy, cardioverter-defibrillator therapy, cardiac rhythm management (CRM) therapy, an electrophysiology (EP) mapping and radio frequency (RF) ablation therapy, electroconvulsive therapy (ECT), repetitive transcranial magnetic stimulation (rTMS) therapy, and vagal nerve stimulation (VNS) therapy, and the like.

FIG. 11 depicts an example test/stimulation program 1100 that may include different pulse settings and patterns including burst and/or tonic stimulation patterns according to one representative embodiment. As illustrated, test/stimulation program 1100 may include test/stim sets SS1-SS7 as belonging to the test program. Accordingly, when test program 1100 is executed by an IMD (e.g., IMD 1000) in response to a mode selection control signal operative to select STM, current pulses may be generated, e.g., as a pulse sequence, according to the parameters of the test/stim sets. Test/stimulation program 1100 may also define the frequency for the test/stimulation program, e.g., 40 Hz, although any suitable frequency could be selected. In one arrangement, appropriate stimuli, e.g., burst stimulus and/or tonic stimulus, as defined by the test/stim sets of the program 1100 may be repeated according to the defined frequency parameter.

Figure 14A:
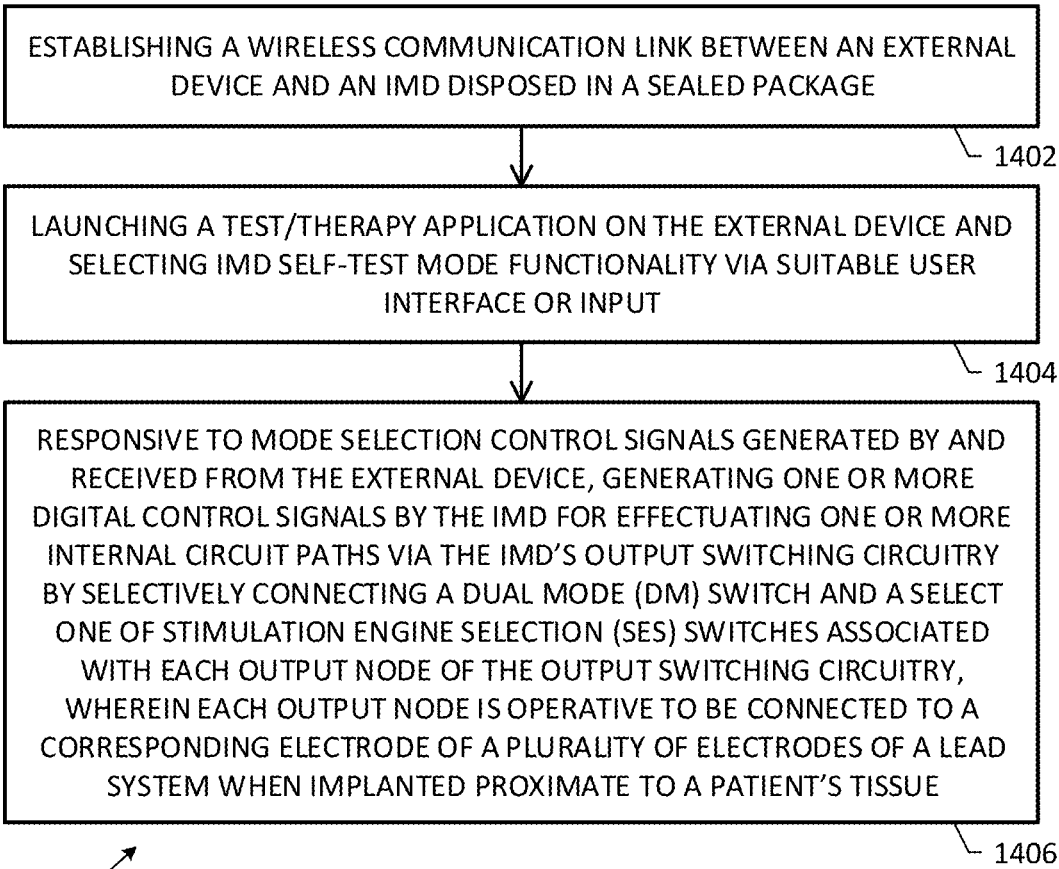
FIGS. 14A and 14B depict flowcharts of blocks, steps and/or acts that may be (re)combined in one or more arrangements for operating an IMD in self-test mode according to some embodiments of the present disclosure.
Figure 14B:
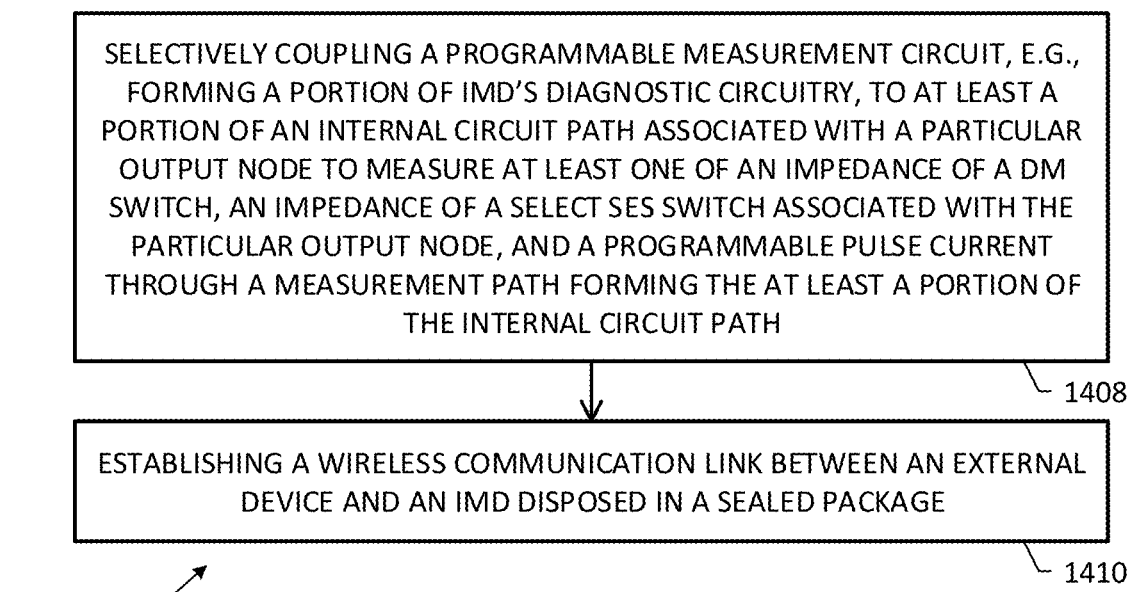

Turning to FIGS. 14A and 14B, depicted therein are flowcharts of blocks, steps and/or acts that may be (re)combined in one or more arrangements for facilitating and operating an IMD in self-test mode according to some embodiments of the present disclosure. Example process 1400A may commence with establishing a wireless communication link between an external device and an IMD disposed in a sealed package, as set forth at block 1402. At block 1404, a therapy and/or test application may be launched on the external device (e.g., depending on the functionality of the external device and/or authorization levels of the user as noted previously), wherein IMD self-test mode functionality may be selected via suitable user interface or input. Responsive to one or more mode selection control signals generated by and received from the external device, one or more digital control signals may be generated by the IMD for effectuating one or more internal circuit paths via the IMD's output switching circuitry by selectively connecting a dual mode (DM) switch and a select stimulation engine selection (SES) switch of a plurality of SES switches associated with each output node of the output switching circuitry, wherein each output node is operative to be connected to a corresponding electrode of a plurality of electrodes of a lead system when implanted proximate to a patient's tissue, as set forth at block 1406.

Example process 1400B may involve selectively coupling a programmable measurement circuit, e.g., a circuit forming a portion of IMD's diagnostic circuitry, to at least a portion of an internal circuit path associated with a particular output node to measure at least one of an impedance of a DM switch, an impedance of a select SES switch associated with the particular output node, and/or a programmable pulse current through a measurement path forming the at least a portion of the internal circuit path (block 1408). One or more measurements obtained from the measurement circuit may be transmitted via the wireless M2M communication link to the external device for presentation thereat via suitable display or UI (block 1410).

Figure 15:
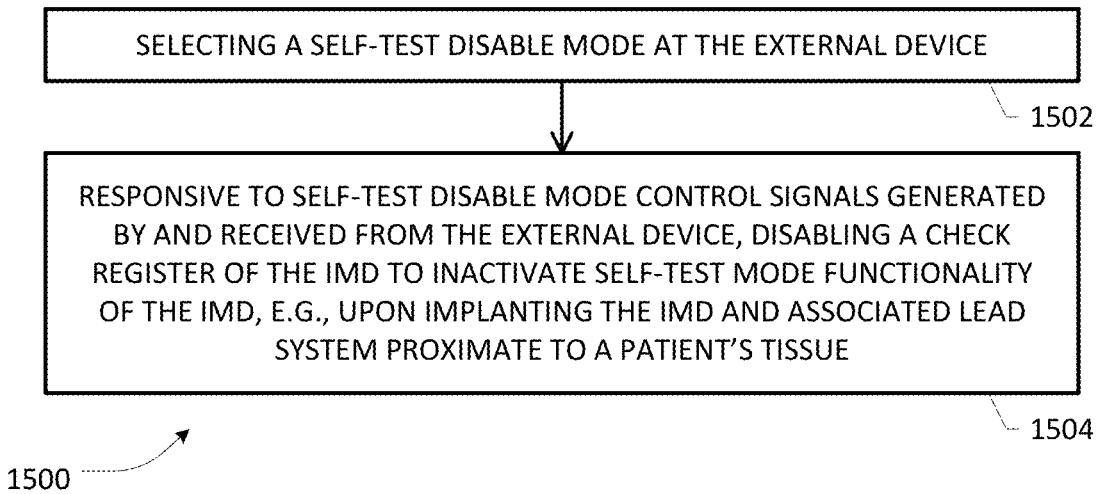
FIGS. 15 and 16 depict flowcharts of blocks, steps and/or acts that may be (re)combined in one or more arrangements and/or with other flowcharts of the present disclosure according to some embodiments.
Figure 16:
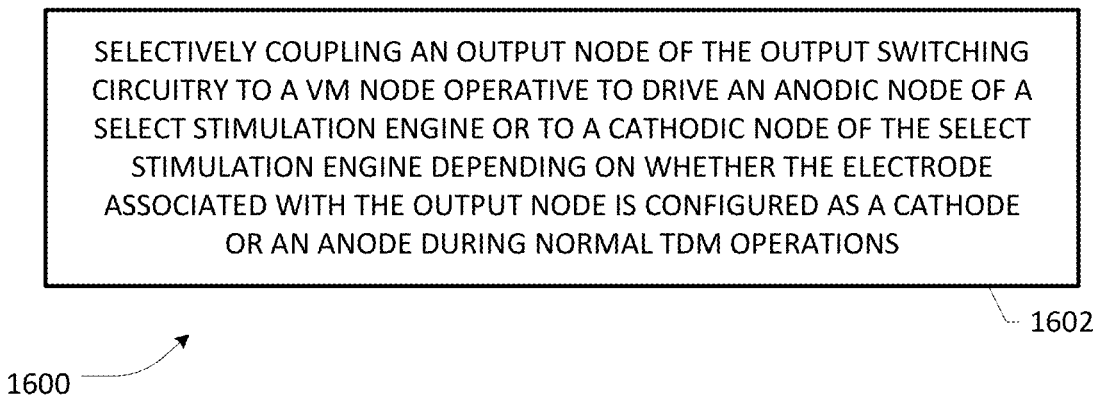

FIGS. 15 and 16 depict flowcharts of blocks, steps and/or acts that may be (re)combined in one or more arrangements and/or with other flowcharts of the present disclosure according to some additional and/or alternative embodiments. Example process 1500 may involve selecting or activating a self-test disable mode at an external device for optionally, selectively and/or temporarily inactivating STM functionality in an IMD (block 1502). Responsive to one or more self-test disable mode control signals generated by and received from the external device, a check register of the IMD may be actuated or written to in order to inactivate STM functionality of the IMD, e.g., upon implanting the IMD and associated lead system proximate to a patient's tissue, whereby another intentional input from an authorized user may be required for (re)enabling STM capability in some example embodiments (block 1504).

It will be recognized that when STM capability is activated by an external tester device (which could be a clinician programmer device (CPD) operated by a clinician in the field, a third-party device authorized to service/test the IMD, a tester used by the IMD manufacturer, etc.), the IMD may still be disposed inside its hermetically sealed package. After the IMD is implanted in a patient, there may be no further need to enable/activate the STM of the IMD again in some example implementations (i.e., the STM capability may be permanently disabled). Until the implant, a packaged IMD may be put into STM one or several times. After the IMD is removed from its package, there may be access to the IMD's header connector that can be used for testing by connecting to an external load even before implanting. In such a scenario, testing is not limited to just the internal circuit paths via the output switching elements but may involve a broader range of tests and measurements.

In a further implementation, STM functionality may continue to be made available even after the IMD is implanted in a patient. Some example scenarios where such a continued access to STM functionality might be useful would be testing at higher voltage levels than the patient can tolerate in order to troubleshoot particular components at the process corners (without actually stimulating the tissue because the measurement paths will be internal to the output switching circuitry rather than via the ETI load). A further example scenario that allows continued STM access after implanting the IMD might be where it is desirable to have additional capabilities, e.g., the ability to recalibrate an impedance measurement in an implanted device, the ability to confirm open circuit warnings, and the like.

Example process 1600 sets forth a high level operation with respect to coupling a select output node during normal TDM operations. In one arrangement, an output node of the output switching circuitry may be selectively coupled to a VM node operative to drive an anodic node of a select stimulation engine or to a cathodic node of the select stimulation engine depending on whether the electrode associated with the output node is configured as a cathode or an anode during normal operations, as set forth at block 1602. If independent and/or variable VM nodes are provided with respect to different SEs, additional switching elements may be provided as part of the output switch matrix as noted previously.

Figure 17A:
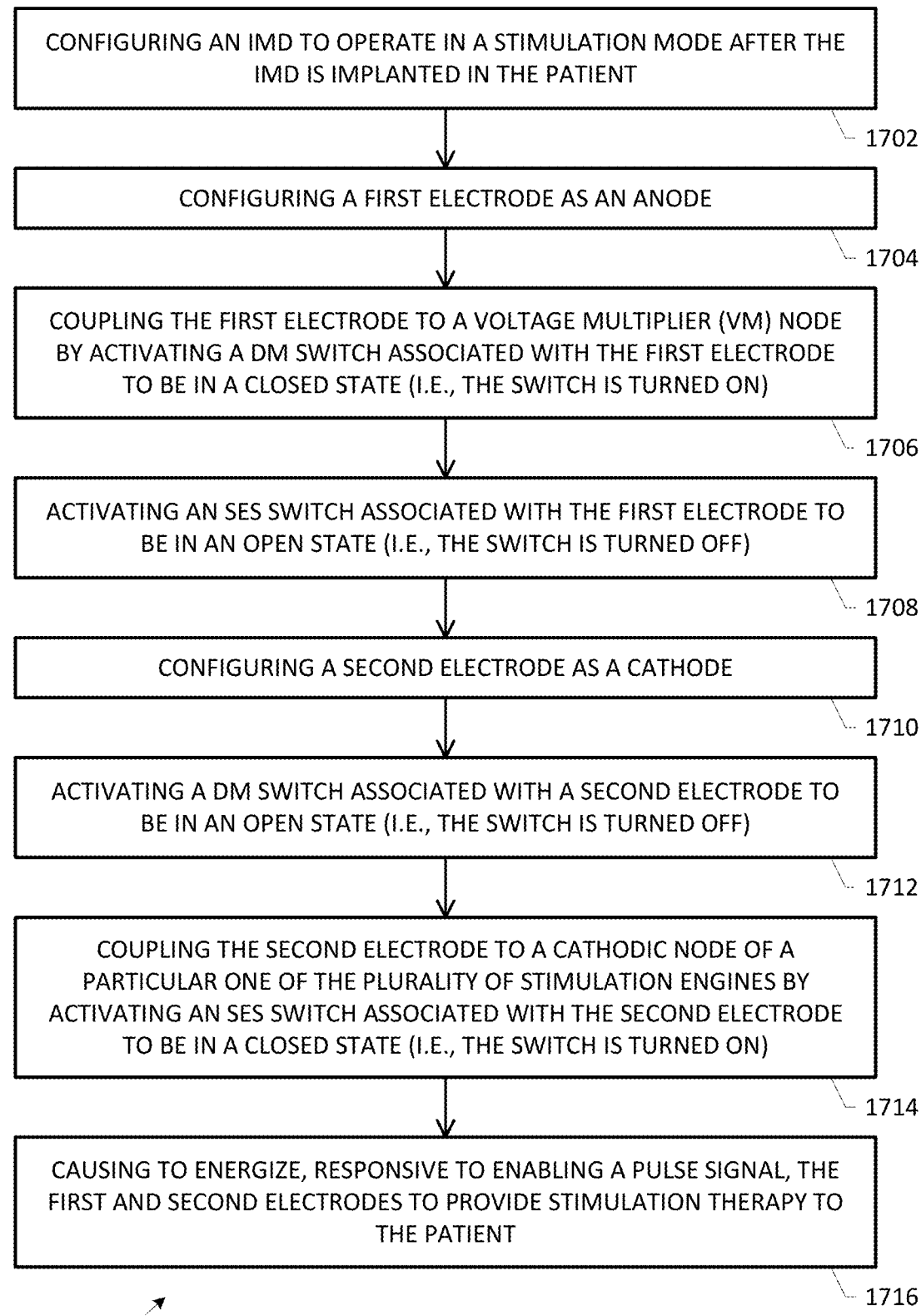
FIGS. 17A and 17B depict flowcharts of blocks, steps and/or acts associated with stimulation and discharge mode functionalities of an IMD according to some embodiments of the present disclosure.
Figure 17B:
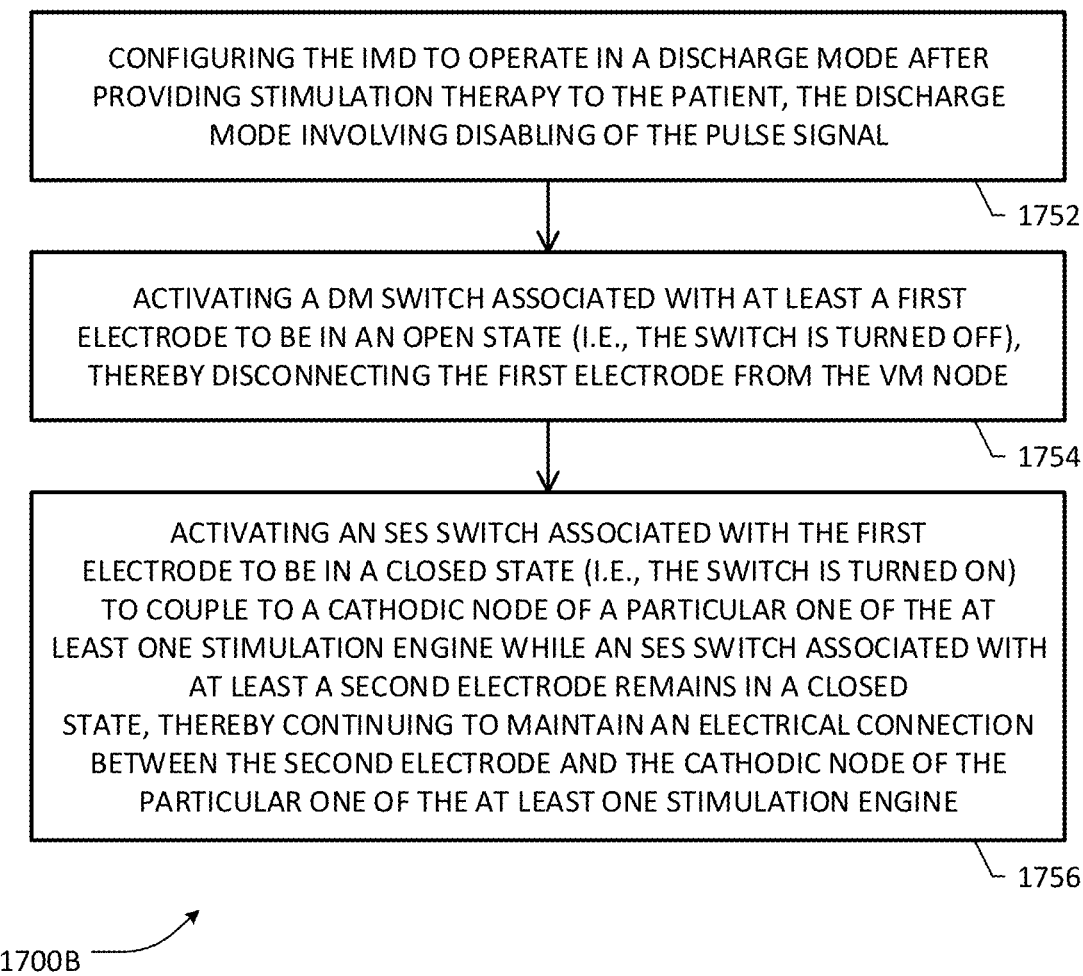

FIGS. 17A and 17B depict flowcharts of blocks, steps and/or acts associated with stimulation and discharge mode functionalities of an IMD according to some embodiments of the present disclosure. Example process 1700A may commence with configuring the IMD to operate in a stimulation mode after the IMD is implanted in a patient (block 1702). At block 1704, a first electrode may be configured as an anode. At block 1706, the first electrode may be coupled to a VM node driven by an adjustable voltage multiplier that may be configured as a charge pump to provide a range of voltages. As noted previously, the VM node coupling may be effectuated by activating a DM switch (e.g., a first DM switch) associated with the first electrode to be in a closed state (i.e., the switch is turned on). At block 1708, a first SES switch associated with the first electrode may be activated to be in an open state (i.e., the switch is turned off). At block 1710, a second electrode may be configured as a cathode. At block 1712, a DM switch associated with a second electrode (i.e., a second DM switch) may be activated to be in an open state (i.e., the switch is turned off). At block 1714, the second electrode may be coupled to a cathodic node of a particular one of the plurality of stimulation engines by activating an SES switch associated with the second electrode (i.e., a second SES switch) to be in a closed state (i.e., the switch is turned on). At block 1716, the first and second electrodes may be caused to provide stimulation therapy to the patient according to a stimulation program by setting appropriate pulse control and timing signals as set forth previously.

Example process 1700B of FIG. 17B may commence with configuring an IMD to operate in a discharge mode after providing stimulation therapy to the patient, wherein the discharge mode may involve disabling of pulse control signals that may have been enabled in order to facilitate providing therapy via at least a pair of electrodes, e.g., first and second electrodes (block 1752). At block 1754, a DM switch associated with the first electrode may be activated to be in an open state (i.e., the switch is turned off), thereby causing to disconnect the first electrode from the VM node. At block 1756, an SES switch associated with the first electrode may be activated to be in a closed state (i.e., the switch is turned on) to couple to the cathodic node of the particular one of the at least one stimulation engine while an SES switch associated with the second electrode remains in the closed state, thereby continuing to maintain an electrical connection between the second electrode and the cathodic node of the particular one of the at least one stimulation engine. As noted previously, appropriate discharge timing control signals may be provided in an example arrangement in accordance with a select discharging program or setting.

Figure 18:
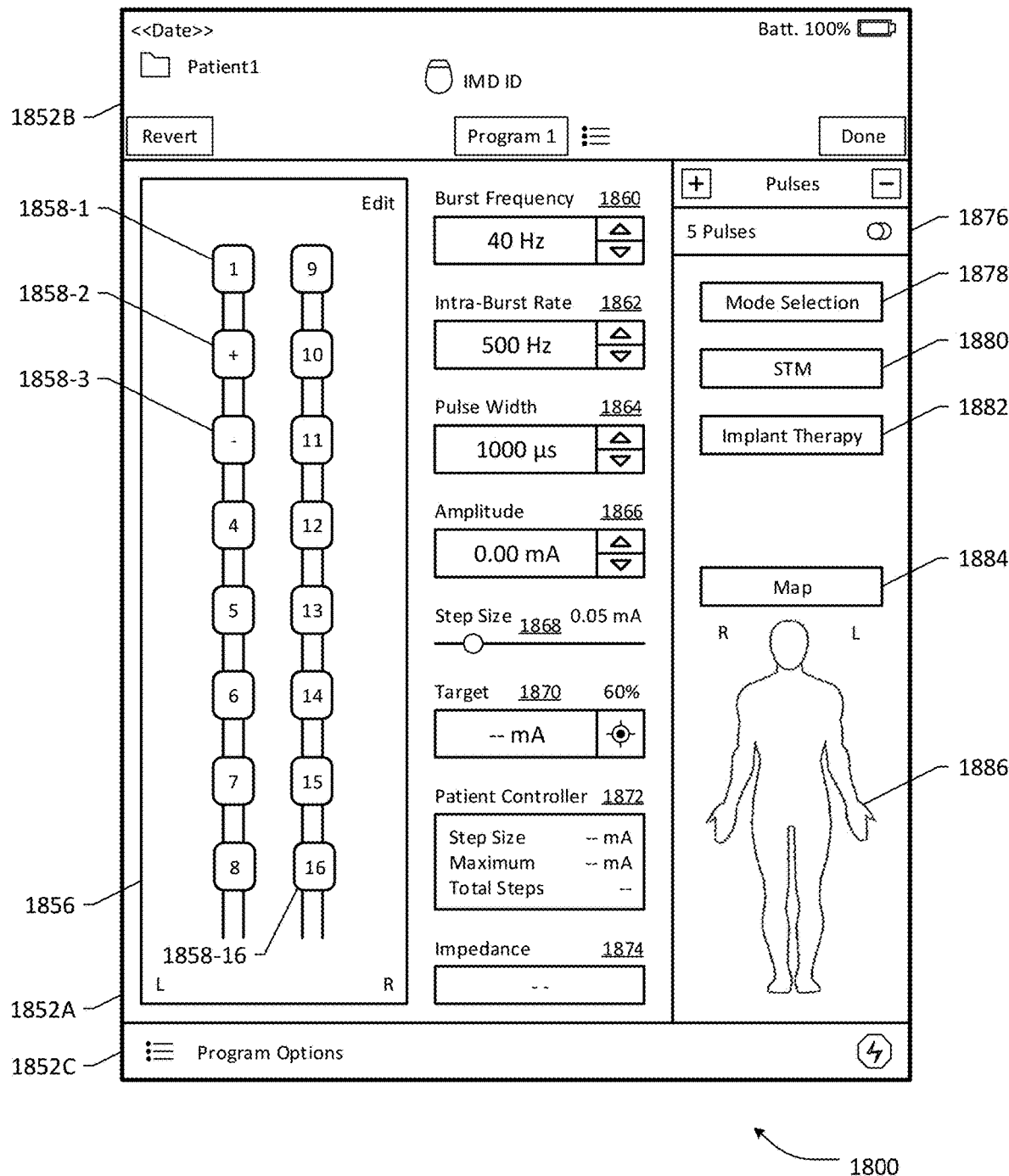
FIG. 18 depicts a user interface (UI) of an external device operative to effectuate mode control and test selection in a packaged IMD according to an example embodiment of the present disclosure.

FIG. 18 depicts a user interface (UI) 1800 of an external device operative to effectuate mode control and test selection in a packaged IMD according to an example embodiment of the present disclosure. UI 1800 may be configured to display one or more panels or windows for presenting various pieces of information, e.g., graphical information, with respect to operating an IMD having configurable output switching circuitry according to the teachings herein. Panel 1852A may include a program options subpanel 1856A and an electrode/output node selection panel 1856B that graphically shows a representation of a plurality of electrodes/output nodes 1858-1 to 1858-16 (e.g., as icons, pictograms, images, etc.) that may be configured to be disposed on one or more leads. For purposes of STM or TDM operations, selected electrodes/output nodes may be suitably highlighted, e.g., electrode/output nodes 1858-2 and 1858-3, whose polarity may be configured as cathodes or anodes. A visualization panel may be effectuated by activating a map button or dialog box 1884 for depicting a representation of the patient, e.g., as a pictogram 1886, which may comprise a bilateral symmetric pictogram showing a left side and a right side of the patient. A window, button or dialog box 1876 may be actuated to select a pulse count (e.g., 5 pulses) that may be scrolled up or down. A mode selection window, button, pull down menu or dialog box 1878 may be activated to effectuate available IMD operational modalities, e.g., STM 1880 for self-test operations in packaged condition or TDM 1882 for therapy and discharge operations in implant condition. A plurality of selection windows, scroll/swipe bars, buttons, pull down menus or dialog boxes may be provided as part of display panel 1856B for specifying/selecting one or more testing/stimulation settings or parameters. By way of example, a burst frequency window 1860, an intra-burst rate window 1862, a pulse width window 1864, an amplitude window 1866, a step size swipe bar 1868, a target current window 1870, and a patient controller window 1872 are illustrated. A results panel 1874 may comprise one or more windows to display appropriate measurement results, e.g., switch impedances, etc., received from the IMD over a wireless M2M communication link. In one arrangement, UI display 1800 may also include an identification panel 1852B that may identify the IMD, selected test/stimulation program, as well as the patient (if the IMD is implanted), among other icons or indicia relating to status indicators etc. Yet another panel 1852C may be provided with respect to selected test/stimulation program options, and the like. Skilled artisans will recognize that the various panels, selection windows, scroll/swipe bars, buttons, pull down menus or dialog boxes, as well as their relative placement, shown herein are purely illustrative and an example UI display may be configured to include more or fewer pieces of information in different display arrangements than are exemplified in FIG. 18.

Based on the foregoing, it should be appreciated that embodiments herein provide a configurable output switching circuit scheme for an IMD that allows a wide range of self-test functionality without requiring an external load or stimulating patient tissue, thereby advantageously facilitating a test modality even when the IMD is still in a sealed package. As such, IMDs may often spend a significant amount of time in storage or transit in a sealed container (e.g., in a hermetically sealed package condition) prior to implanting in a patient. Such a packaged state may be provided so as to maintain sterility and integrity of the device, e.g., by securing the device against water vapor and foreign bodies that can compromise proper functioning and reliability of the IMD. Whereas the capability to test the integrity of output switch functionality of an IMD while it is still its sealed box is quite limited in existing IMD implementations as the essential outputs require a connection to patient tissue or an external load, example embodiments herein advantageously overcome such limitations by facilitating internal circuit paths via the output switching circuitry that can be configured over wireless links for effectuating test measurements relative to the output switch elements. In addition, measurement circuits inside an IMD are often also subject to widely variable offsets due to the output select switches being in between the measurement circuit and patient tissue. However, because there are no patient ETI loads involved, such issues are often absent or advantageously mitigated in example embodiments set forth herein.

Example embodiments also advantageously leverage passive discharge control switching in an IMD for providing STM functionality without requiring additional switch elements. For example, in order to protect against unwanted charge buildup at the interface where a metal electrode contacts patient tissue, an example IMD may be equipped with the ability to passively discharge the electrodes that have been used for stimulation by way of turning on a discharge switch. In some example arrangements, this passive discharge switch may often be either implemented outside the electrode switching circuit or simply connects an electrode to ground or a DC voltage. An example embodiment of the present disclosure is not only compatible with a multi-engine approach to stimulation but is also configurable to place the passive discharge functionality in the electrode selection circuit, e.g., output switching circuitry, of the IMD. Thus, if the device is placed in a TEST mode and a switch is programmed as an anode, then a complete electrical circuit can be formed inside one instance of the electrode switching circuit (i.e., output switching portion) without requiring extra switch circuitry because the same switch can be used in discharging operations by deactivating it under programmatic control. Additional benefits and features of example embodiments may involve one or more of the following. In one arrangement, the passive discharge functionality may be contained in the output select circuitry, which does not require a connection to a fixed reference (e.g., ground or a DC voltage). Passive discharge may be achieved by engine-specific PULSE and DISCHARGE timing signals that control the electrode/output node selection circuits in an example embodiment as set forth above. Furthermore, an example embodiment may be configured to provide one or more following. (1) the ability to ensure all outputs or a portion thereof can be programmed as anodes or cathodes or OFF while the IMD/IPG is in its sealed package; (2) the ability to ensure that all engine current delivery circuits are functional while the IMD/IPG is in its sealed package; (3) the ability to self-calibrate for switch offsets in an implanted device that uses internal measurement circuits, which can be done with no stimulation of patient tissue since the current flow is contained only in the switch circuits; (4) the ability to ensure that stimulation can be delivered from all available supply options while the IMD/IPG is in its sealed package; and (5) ensuring that TEST mode programming cannot be entered unintentionally by requiring a check register verification and/or a multiple bit write operation.

In the above-description of various embodiments of the present disclosure, it is to be understood that the terminology used herein is for the purpose of describing particular embodiments only and is not intended to be limiting of the scope of the claims. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense unless expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, some example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Various types of switching circuit blocks as well as associated control logic signals as set forth in the example embodiments may be implemented in myriad ways using a broad range of electronic devices known in the electrical arts, e.g., including but not limited to bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, diodes, and the like, as well as any digital logic gates built therefrom. It will be further understood that the sizing (e.g., channel width and length) and biasing of the switching devices is highly configurable, e.g., depending on whether anodic current stimulation or cathodic stimulation current is being programmed (i.e., whether the electrodes of a lead system are configured to operate as current sink terminals or cathodes, or as current source terminals or anodes) as well as how much current is to be carried for each electrode set (i.e., granularity and distribution of the currents drawn from respective loads).

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, skilled artisans will appreciate that communication may occur in the opposite direction relative to the depicted arrows. Finally, other blocks may be added/inserted between the blocks that are illustrated. It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. An implantable medical device (IMD), comprising:
a power supply;
one or more processors;
communication circuitry operative to effectuate a machine-to-machine (M2M) communication link with an external device using a wireless communication protocol;
a voltage multiplier (VM) configured to generate an adjustable target voltage at a VM node based on a voltage supplied by the power supply;
at least one stimulation engine operative to energize at least a portion of a plurality of electrodes of a lead system when implanted proximate to a tissue of a patient; and
output switching circuitry operative to drive a plurality of output nodes, each output node connectable to a corresponding electrode of the plurality of electrodes when implanted, the output switching circuitry comprising, for each respective output node a switching portion including:
a dual mode (DM) switch for selectively coupling the respective output node to the VM node operative to power an anodic node of the at least one stimulation engine; and
one or more stimulation engine selection (SES) switches operative to be disposed in a series connection with the DM switch, wherein a select one of the one or more SES switches is configured for selectively coupling the respective output node to a cathodic node of the at least one stimulation engine, and wherein the DM switch and the select one of the one or more SES switches are activated to close so as to effectuate an internal circuit path in the output switching circuitry of the IMD in a self-test mode in response to one or more digital control signals generated under control of the one or more processors operating responsive to a mode selection control signal from the external device while the IMD is disposed in a sealed package condition.

2. The IMD as recited in claim 1, further comprising a programmable measurement circuit having selectable inputs operative to effectuate one or more measurement loops involving at least a portion of the internal circuit path when the IMD is in the self-test mode, wherein the one or more measurement loops comprise, for each respective output node of the output switching circuitry, a measurement path across at least one of the DM switch in a closed state and the select one of the one or more SES switches in a closed state.

3. The IMD as recited in claim 2, wherein the programmable measurement circuit is configured to measure, for each respective output node, at least one of an impedance of the DM switch in the closed state, an impedance of the select one of the one or more SES switches in the closed state, and programmability of a pulse current through the measurement path, the pulse current having configurable pulse settings and patterns selectable from a user interface of the external device.

4. The IMD as recited in claim 1, further comprising a self-test mode check register configured to enable the self-test mode of the IMD responsive to the mode selection control signal from the external device.

5. The IMD as recited in claim 1, wherein the self-test mode check register is configured to be actuated to selectively disable the self-test mode of the IMD when the IMD is implanted in the patient.

6. The IMD as recited in claim 5, wherein, when the IMD is disposed in a stimulation mode after the IMD is implanted in the patient, a first DM switch associated with a first electrode is activated to be in a closed state and a first SES switch associated with the first electrode is activated to be in an open state when the first electrode is configured to be an anode, and further wherein a second DM switch associated with a second electrode is activated to be in an open state and a second SES switch associated with the second electrode is activated to be in a closed state when the second electrode is configured to be a cathode, thereby causing a particular one of the at least one stimulation engine to energize, responsive to enabling a pulse signal, the first and second electrodes to provide stimulation therapy to the patient.

7. The IMD as recited in claim 6, wherein, when the IMD is disposed in a discharge mode after providing stimulation therapy to the patient, the discharge mode involving disabling of the pulse signal, the first DM switch associated with the first electrode is activated to be in an open state and the first SES switch associated with the first electrode is activated to be in a closed state to couple to a cathodic node of the particular one of the at least one stimulation engine while the second SES switch associated with the second electrode remains in the closed state, thereby continuing to maintain an electrical connection between the second electrode and the cathodic node of the particular one of the at least one stimulation engine.

8. The IMD as recited in claim 6, wherein the at least one stimulation engine is operative to provide stimulation therapy including at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

9. The IMD as recited in claim 1, wherein the communication circuitry comprises circuitry for effectuating the M2M communication link using a wireless communication protocol including at least one of Bluetooth Low Energy (BLE), Bluetooth, Wireless USB, Zigbee, Near-Field Communications (NFC), an IEEE 802.11-compliant protocol, Infrared Wireless protocol, induction wireless protocol, Medical Implant Communication Service (MICS) protocol, Wireless Medical Telemetry Service (MTS) protocol, Medical Device Radiocommunications Service (MDRS) protocol, and Medical Data Service (MDS) protocol.

* * * * *

UNITED STATES PATENT AND TRADEMARK OFFICE
CERTIFICATE OF CORRECTION

PATENT NO. : 11,969,600 B2
APPLICATION NO. : 17/355677
DATED : April 30, 2024
INVENTOR(S) : DeShazo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
Eighth Day of October, 2024

Katherine Kelly Vidal
*Director of the United States Patent and Trademark Office*